United States Patent
Haight et al.

(10) Patent No.: US 10,058,388 B2
(45) Date of Patent: *Aug. 28, 2018

(54) LASER SURGICAL APPARATUS AND METHODS OF ITS USE MINIMIZING DAMAGE DURING THE ABLATION OF TISSUE USING A FOCUSED ULTRASHORT PULSED LASER BEAM WHEREIN THE SLOPE OF FLUENCE BREAKDOWN IS A FUNCTION OF THE PULSE WIDTH

(71) Applicant: GLOBALFOUNDRIES INC., Grand Cayman (KY)

(72) Inventors: Richard Alan Haight, Mahopac, NY (US); Peter P Longo, Hopewell Junction, NY (US); Daniel P Morris, Purchase, NY (US); Alfred Wagner, Brewster, NY (US)

(73) Assignee: GLOBALFOUNDRIES INC., Grand Cayman (KY)

( * ) Notice: Subject to any disclaimer, the term of this patent is extended or adjusted under 35 U.S.C. 154(b) by 216 days.

This patent is subject to a terminal disclaimer.

(21) Appl. No.: 14/730,503

(22) Filed: Jun. 4, 2015

(65) Prior Publication Data

US 2015/0265351 A1    Sep. 24, 2015

Related U.S. Application Data

(60) Continuation of application No. 13/735,394, filed on Jan. 7, 2013, now abandoned, and a continuation of
(Continued)

(51) Int. Cl.
*A61B 18/20* (2006.01)
*A61F 9/008* (2006.01)
(Continued)

(52) U.S. Cl.
CPC .............. *A61B 18/20* (2013.01); *A61B 18/26* (2013.01); *A61F 9/0084* (2013.01);
(Continued)

(58) Field of Classification Search
CPC ....... A61B 18/20; A61B 18/203; A61B 18/26; A61B 2018/00452; A61B 2018/0047;
(Continued)

(56) References Cited

U.S. PATENT DOCUMENTS 4,907,586 A    3/1990  Bille et al.
5,656,186 A    8/1997  Mourou et al.
(Continued)

OTHER PUBLICATIONS

Office Action dated Sep. 15, 2015, received in a related U.S. Appl. No. 13/735,394.

*Primary Examiner* — Boniface N Nganga
(74) *Attorney, Agent, or Firm* — Scully Scott Murphy and Presser; Frank S. Digiglio

(57) ABSTRACT

A laser apparatus for use in a surgical procedure is disclosed including a housing forming a part of a handpiece and including interior and exterior regions, a laser cavity extending within the interior region of the housing, at least a portion of an operating laser element positioned with the interior region of the housing for generating an operating beam, and a controller to control a focal position of the operating beam to a location above the plane of the tissue for ablation of the tissue by laser induced breakdown thereof.

20 Claims, 24 Drawing Sheets

Related U.S. Application Data application No. 12/545,216, filed on Aug. 21, 2009, now Pat. No. 8,389,890, and a division of application No. 09/933,461, filed on Aug. 20, 2001, now Pat. No. 7,649,153, and a continuation-in-part of application No. 09/210,226, filed on Dec. 11, 1988, now Pat. No. 6,333,485.

(51) Int. Cl.
| | |
|---|---|
| *A61B 18/26* | (2006.01) |
| *G03F 1/72* | (2012.01) |
| *B23K 26/0622* | (2014.01) |
| *B23K 26/066* | (2014.01) |
| *B23K 26/362* | (2014.01) |
| *B23K 26/40* | (2014.01) |
| *B23K 26/402* | (2014.01) |
| *B23K 103/00* | (2006.01) |
| *A61B 18/00* | (2006.01) |

(52) U.S. Cl.
CPC ........ *A61F 9/00814* (2013.01); *B23K 26/066* (2015.10); *B23K 26/0624* (2015.10); *B23K 26/362* (2013.01); *B23K 26/40* (2013.01); *B23K 26/402* (2013.01); *G03F 1/72* (2013.01); *A61B 18/203* (2013.01); *A61B 2018/00577* (2013.01); *A61B 2018/00625* (2013.01); *A61F 2009/00863* (2013.01); *B23K 2203/30* (2015.10); *B23K 2203/50* (2015.10)

(58) Field of Classification Search
CPC .. A61B 2018/00476; A61B 2018/2025; A61B 2017/00057; A61B 2017/00747; A61F 9/00814; A61F 2009/00863; B23K 26/0624; B23K 26/066; B23K 26/362; B23K 26/40; B23K 26/402; B23K 26/401; B23K 26/4075; B23K 2203/30; B23K 2203/50; G03F 1/72; G03F 1/0092
See application file for complete search history.

(56) References Cited

U.S. PATENT DOCUMENTS

| | | | | |
|---|---|---|---|---|
| 5,868,731 | A * | 2/1999 | Budnik | A61B 18/203 606/13 |
| 6,231,567 | B1 * | 5/2001 | Rizoiu | A61B 18/26 606/10 |
| 6,251,102 | B1 * | 6/2001 | Gruzdev | A61B 18/203 372/34 |
| 6,333,485 | B1 * | 12/2001 | Haight | A61B 18/26 219/121.68 |
| 7,649,153 | B2 * | 1/2010 | Haight | A61B 18/26 219/121.69 |
| 8,389,890 | B2 * | 3/2013 | Haight | A61B 18/26 219/121.69 |
| 9,083,557 | B2 | 7/2015 | Bansal et al. | |
| 2011/0314106 | A1 | 12/2011 | Bansal et al. | |
| 2015/0074212 | A1 | 3/2015 | Bansal et al. | |

* cited by examiner

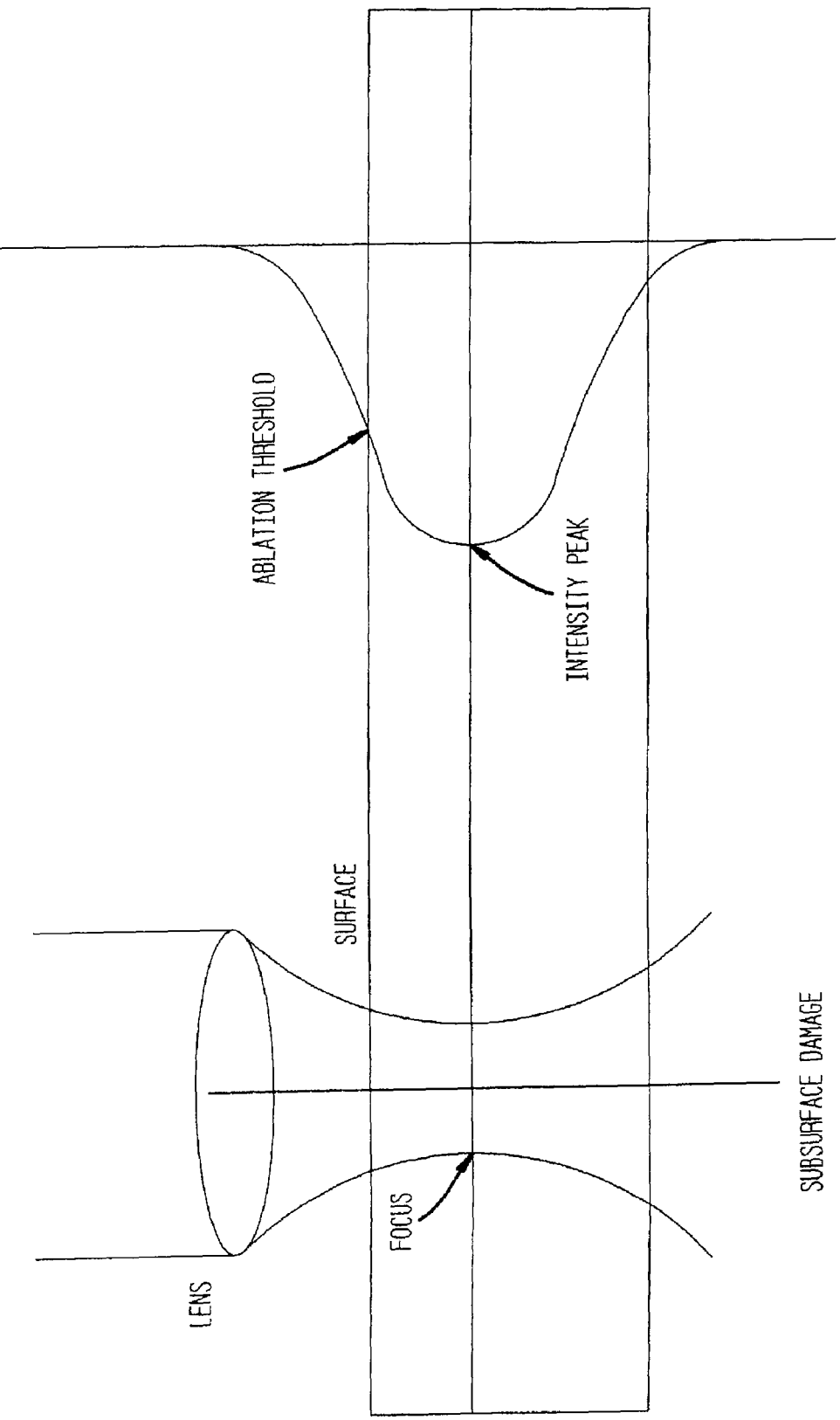

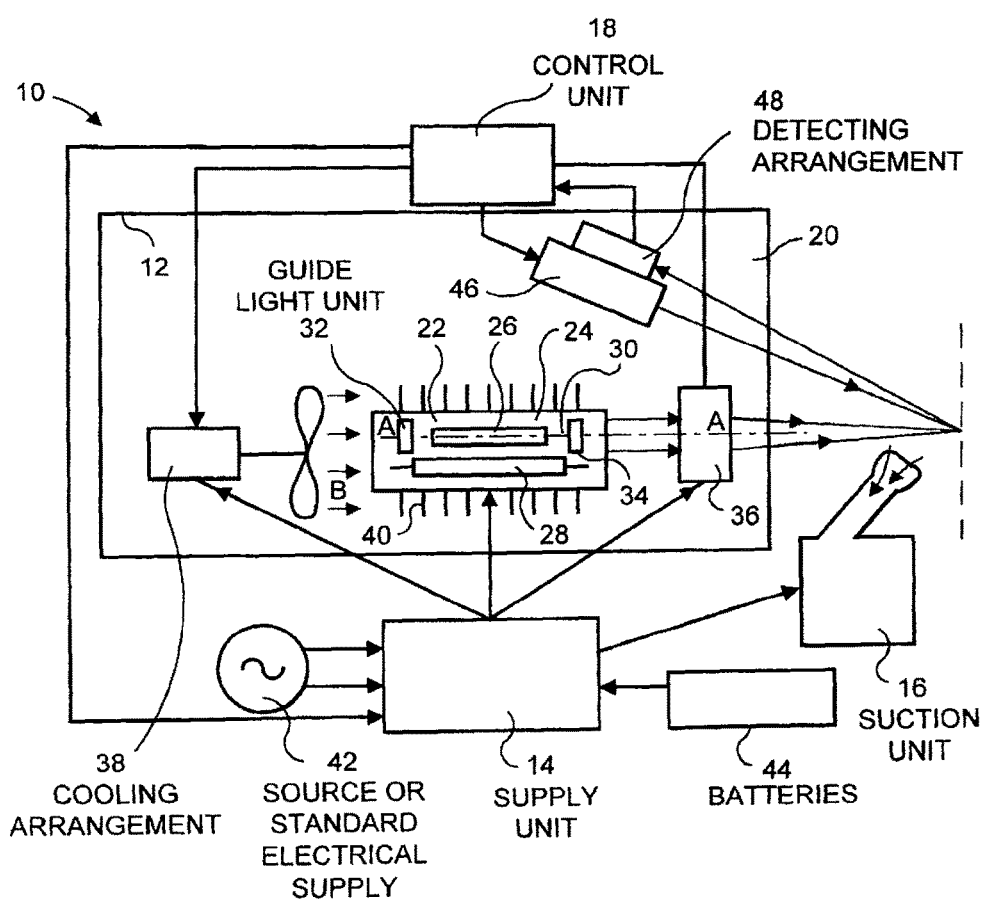
F I G. 17

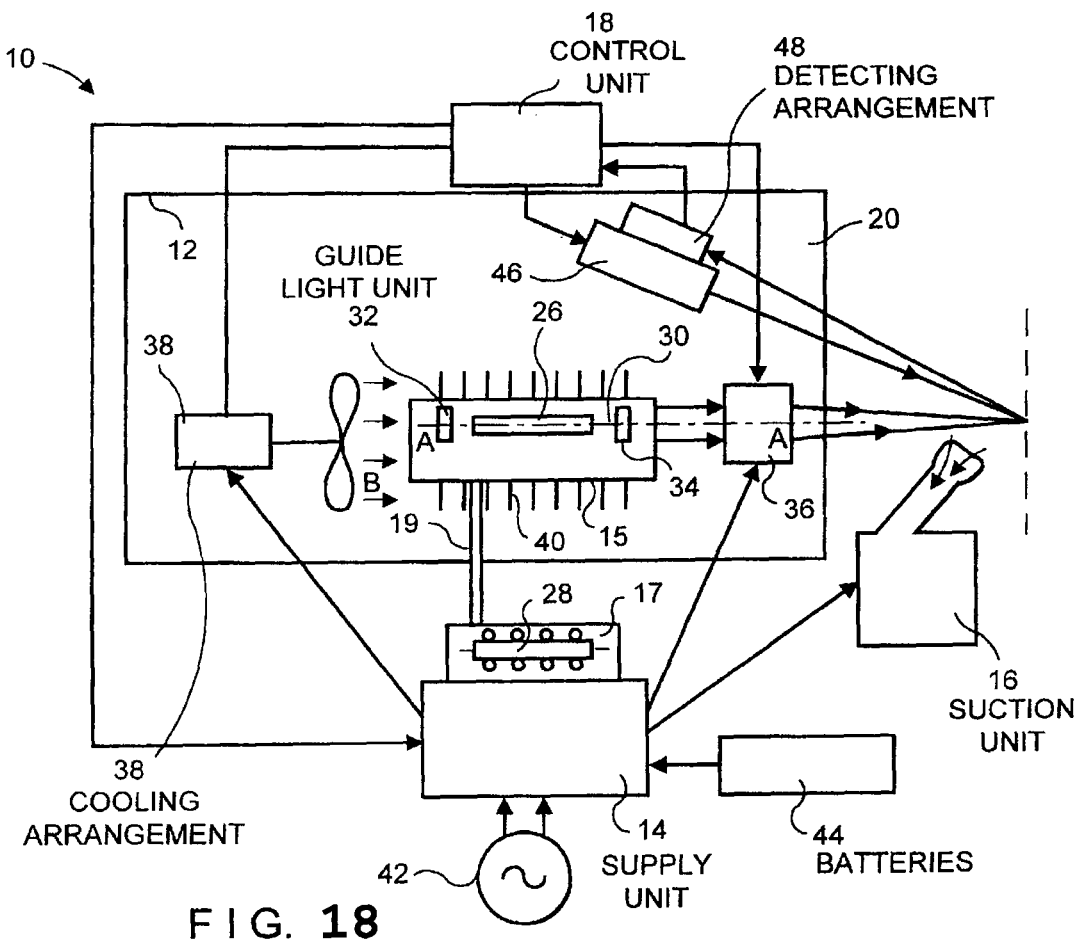
F I G. 18
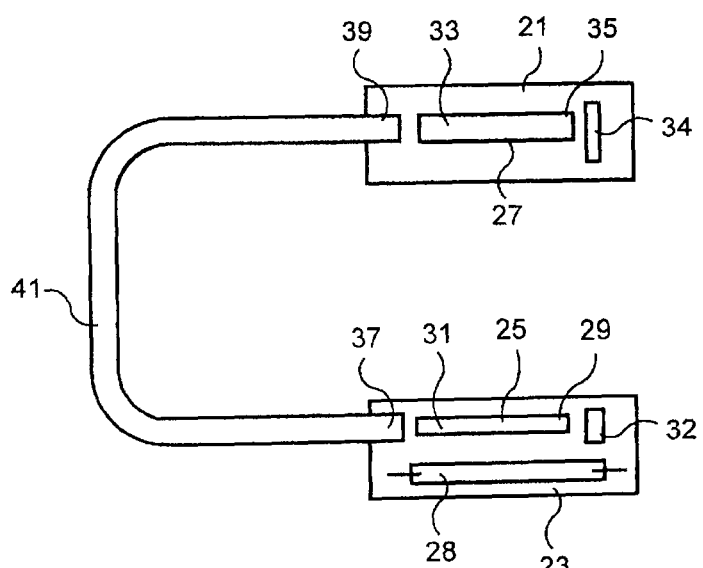
F I G. 19

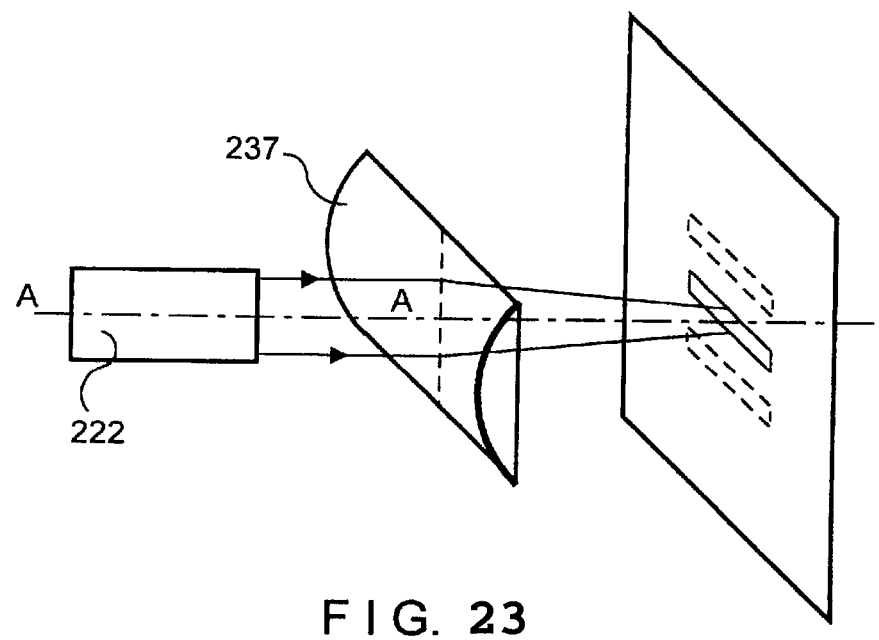
F I G. 23
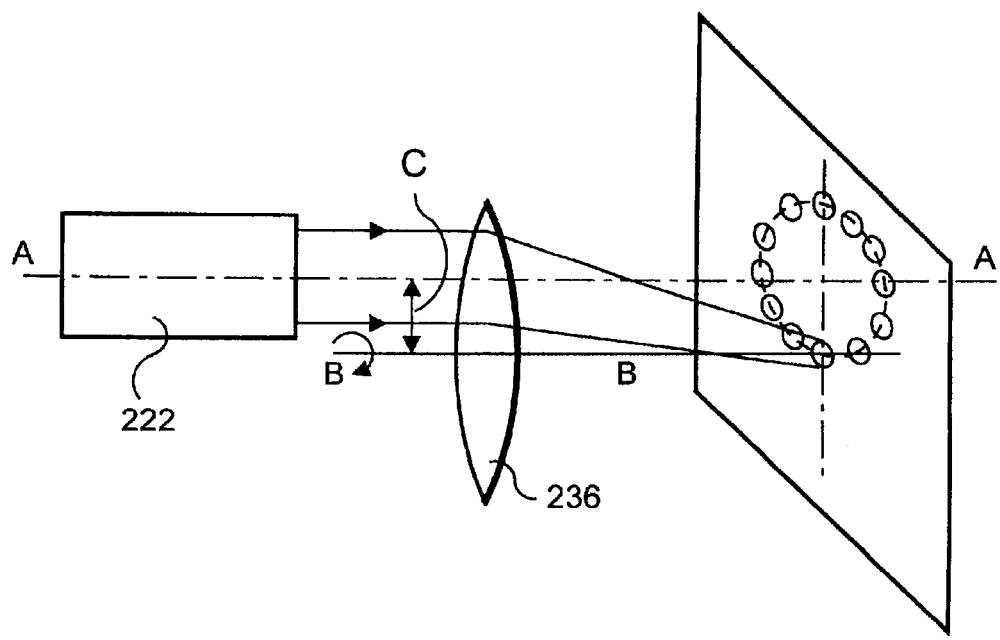
F I G. 24

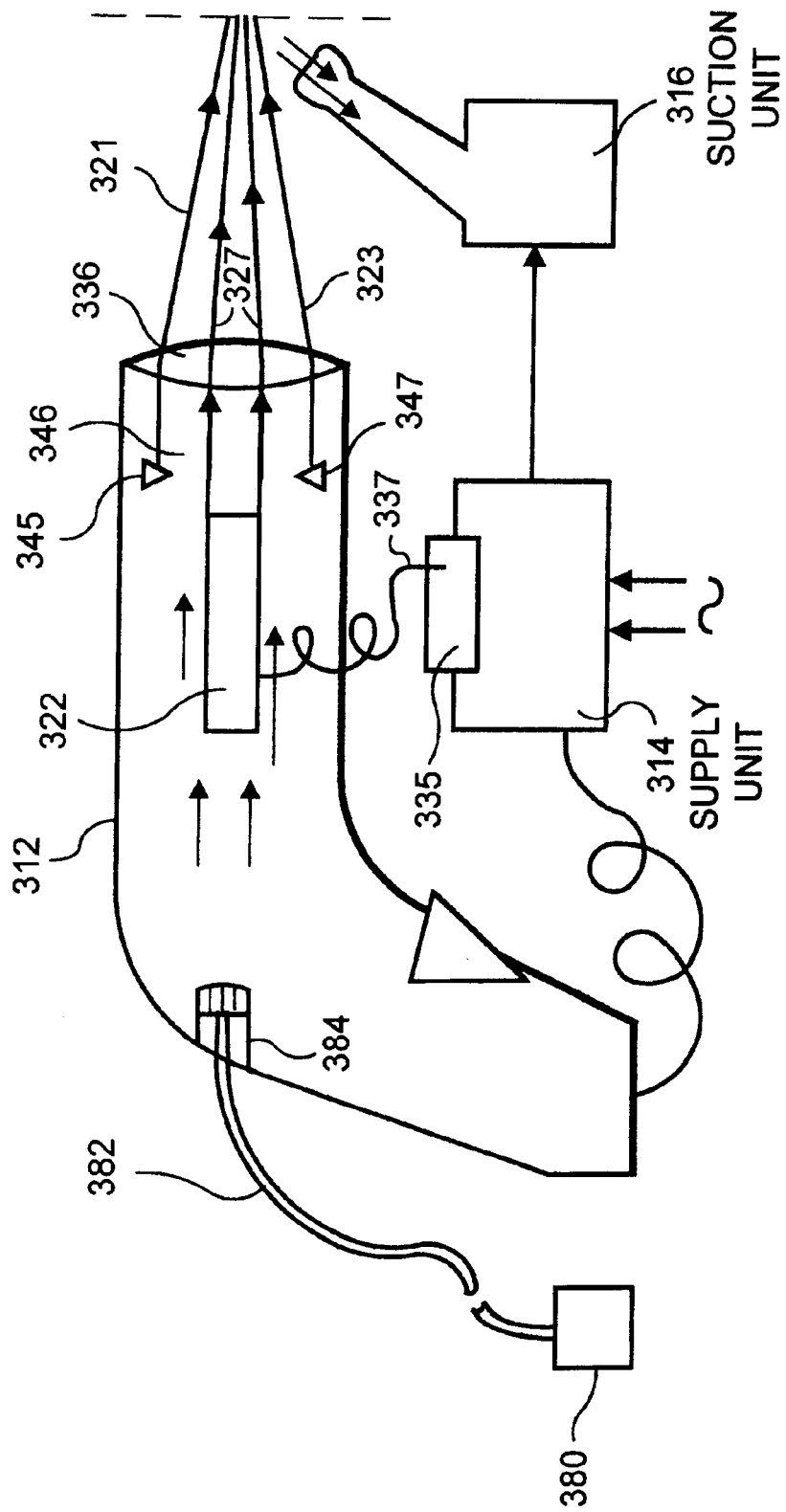
F I G. 34

LASER SURGICAL APPARATUS AND METHODS OF ITS USE MINIMIZING DAMAGE DURING THE ABLATION OF TISSUE USING A FOCUSED ULTRASHORT PULSED LASER BEAM WHEREIN THE SLOPE OF FLUENCE BREAKDOWN IS A FUNCTION OF THE PULSE WIDTH

FIELD OF THE INVENTION

This invention relates generally to laser surgical apparatus methods if its minimizing damage during the ablation of tissue using a focused ultrashort pulsed laser beam wherein the slope of the fluence breakdown is a function of pulse width.

BACKGROUND OF THE INVENTION

Laser induced breakdown of a material causes chemical and physical changes, chemical and physical breakdown, disintegration, ablation, and vaporization. Lasers provide good control for procedures which require precision such as inscribing a micro pattern. Pulsed rather than continuous beams are more effective for many procedures, including medical procedures. A pulsed laser beam comprises bursts or pulses of light which are of very short duration, for example, on the order of 10 nanoseconds in duration or less. Typically, these pulses are separated by periods of quiescence. The peak power of each pulse is relatively high often on the order of gigawatts and capable of intensity on the order of $10^{13}$ w/cm2. Although the laser beam is focused onto an area having a selected diameter, the effect of the beam extends beyond the focused area or spot to adversely affect peripheral areas adjacent to the spot. Sometimes the peripheral area affected is several times greater than the spot itself. This presents a problem, particularly where tissue is affected in a medical procedure. In the field of laser machining, current lasers using nanosecond pulses cannot produce features with a high degree of precision and control, particularly when nonabsorptive wavelengths are used.

It is a general object to provide a method to localize laser induced breakdown. Another object is to provide a method to induce breakdown in a preselected pattern in a material or on a material.

U.S. Pat. No. 5,656,186 to Mourou et al. is directed to a method for laser-induced breakdown. The teaching of Mourou et al. requires that the laser beam be focused to a point at or beneath the surface from which material is to be removed. Applicants have discovered that it is undesirable to focus at or beneath the surface since this results in undesired damage beneath the surface, in particular to the substrate (or underlayer) on which the material that is to be removed is disposed. This is particularly a problem where the underlayer is very sensitive to the laser light and/or can be easily damaged by the laser light. Applicants have unexpectedly discovered that the light source should be focused above the surface to be removed toward this undesired change.

SUMMARY OF THE INVENTION

In one aspect the invention provides a method for laser induced breakdown of a material with a pulsed laser beam where the material is characterized by a relationship of fluence breakdown threshold (Fth) versus laser beam pulse width (T) that exhibits an abrupt, rapid, and distinct change or at least a clearly detectable and distinct change in slope at a predetermined laser pulse width value. The method generating a beam of laser pulses in which each pulse has a pulse width equal to or less than the predetermined laser pulse width value. The beam is focused to a point above the surface of a material where laser induced breakdown is desired. The beam is focused to have the region of least confusion above the surface of a material where laser-induced breakdown is desired.

In one aspect, the invention may be understood by further defining the predetermined laser pulse width as follows: the relationship between fluence breakdown threshold and laser pulse defines a curve having a first portion spanning a range of relatively long (high) pulse width where fluence breakdown threshold (Fth) varies with the square root of pulse width ($T^{1/2}$). The curve has a second portion spanning a range of short (low) pulse width relative to the first portion. The proportionality between fluence breakdown threshold and pulse width differ in the first and second portions of the curve and the predetermined pulse width is that point along the curve between its first and second portions. In other words, the predetermined pulse width is the point where the Fth versus $\tau_p$ relationship no longer applies, and, of course, it does not apply for pulse widths shorter than the predetermined pulse width.

The scaling of fluence breakdown threshold (Fth) as a function of pulse width (T) is expressed as Fth proportional to the square root of $T^{1/2}$ is demonstrated in the pulse width regime to the nanosecond range. The invention provides methods for operating in pulse widths to the picosecond and femtosecond regime where we have found that the breakdown threshold (Fth) does not vary with the square root of pulse width ($T^{1/2}$).

Pulse width duration from nanosecond down to the femtosecond range is accomplished by generating a short optical pulse having a predetermined duration from an optical oscillator. Next the short optical pulse is stretched in time by a factor of between about 500 and 10,000 to produce a timed stretched optical pulse to be amplified. Then, the time stretched optical pulse is amplified in a solid state amplifying media. This includes combining the time stretched optical pulse with an optical pulse generated by a second laser used to pump the solid state amplifying media. The amplified pulse is then recompressed back to its original pulse duration.

In one embodiment, a laser oscillator generates a very short pulse on the order of 10 to 100 femtoseconds at a relatively low energy, on the order of 0.001 to 10 nanojoules. Then, it is stretched to approximately 100 picoseconds to 1 nanosecond and 0.001 to 10 nanojoules. Then, it is amplified to typically on the order of 0.001 to 1,000 millijoules and 100 picoseconds to 1 nanosecond and then recompressed. In its final state it is 10 to 200 femtoseconds and 0.001 to 1,000 millijoules. Although the system for generating the pulse may vary, it is preferred that the laser medium be sapphire which includes a titanium impurity responsible for the lasing action.

In one aspect, the method of the invention provides a laser beam which defines a spot that has a lateral gaussian profile characterized in that fluence at or near the center of the beam spot is greater than the threshold fluence whereby the laser induced breakdown is ablation of an area within the spot. The maximum intensity is at the very center of the beam waist. The beam waist is the point in the beam where wave-front becomes a perfect plane; that is, its radius of curvature is infinite. This center is at radius R=0 in the x-y axis and along the Z axis, Z=0. This makes it possible to damage material in a very small volume Z=0, R=0. Thus it is possible to make features smaller than spot size in the x-y focal plane and smaller than the Rayleigh range (depth of focus) in the Z axis. It is preferred that the pulse width duration be in the femtosecond range although pulse duration of higher value may be used so long as the value is less than the pulse width defined by an abrupt or discernable change in slope of fluence breakdown threshold versus laser beam pulse width.

In another aspect, a diaphragm, disk, or mask is placed in the path of the beam to block at least a portion of the beam to cause the beam to assume a desired geometric configuration. In still further aspects, desired beam configurations are achieved by varying beam spot size or through Fourier Transform (FT) pulse shaping to cause a special frequency distribution to provide a geometric shape.

It is preferred that the beam have an energy in the range of 10 nJ (nanojoules) to 1 millijoule and that the beam have a fluence in the range of 0.1 J/cm2 to 100 J/cm2 (joules per centimeter square). It is preferred that the wavelength be in a range of 200 nm (nanometers) to 1 urn (micron).

Advantageously, the invention provides a new method for determining the optimum pulse width duration regime for a specific material and a procedure for using such regime to produce a precisely configured cut or void in or on a material. For a given material the regime is reproducible by the method of the invention. Advantageously, very high intensity results from the method with a modest amount of energy and the spot size can be very small. Damage to adjoining area is minimized which is particularly important to human and animal tissue.

These and other object features and advantages of the invention will be become apparent from the following description of the preferred embodiments, claims, and accompanying drawings.

BRIEF DESCRIPTION OF THE DRAWINGS

FIG. 14b shows a light source focused beneath the surface of the layer to be ablated.

FIG. 17 shows one embodiment of a laser surgical device of the invention;

FIG. 18 shows another embodiment of the laser surgical device;

FIG. 19 shows a portion of a further embodiment of the laser surgical device;

FIG. 23 shows a laser surgical device having substantially cylindrical focusing lens;

FIG. 24 shows a laser surgical device with the focusing lens movable about shifted axis;

FIG. 34. shows a further cooling arrangement of the invention;

DETAILED DESCRIPTION

Figure 1:
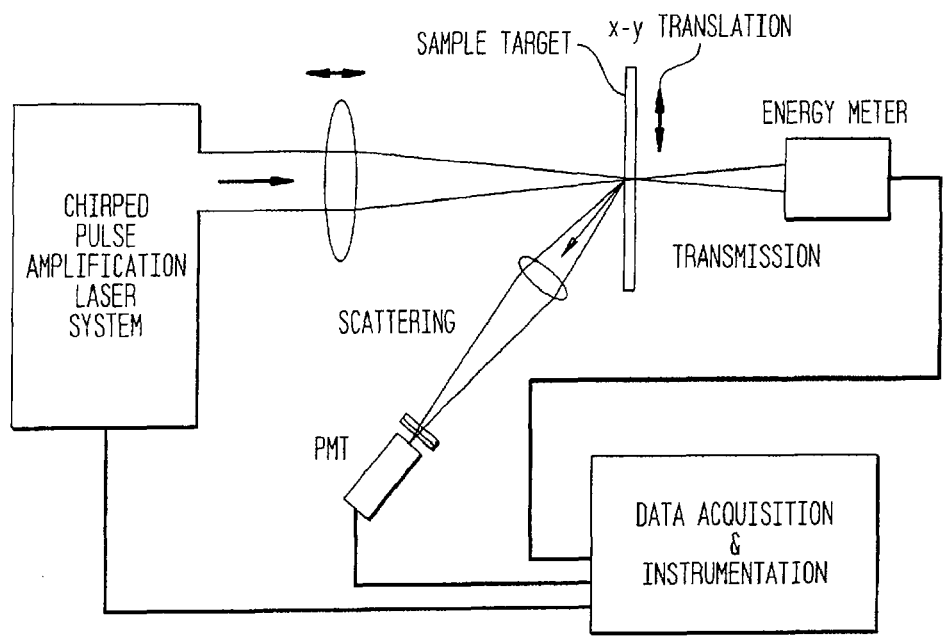
FIG. 1 is a schematic representation of a laser induced breakdown experimental system which includes a chirped pulse amplification laser system and means for detecting scattered and transmitted energy. If the sample is transparent, then transmitted energy can also be measured.

Pulses of light emitted by a laser are capable of removing material from a sample. Typically, the light is focused onto the surface of the sample to both 1) increase the intensity of the light and 2) localize the region of material removal. We have found that it is particularly advantageous to focus the laser beam above the surface of the material to be ablated, rather than focusing at or below the surface. In any situation where material must be removed from the surface without risking damage or ablation of the underlying substrate, our focusing technique is crucial. By focusing above the surface, the maximum intensity of laser light occurs away from the sample. The light intensity then decreases monotonically as the laser beam moves toward and into the sample (see FIG. 14a). This procedure ensures that the laser intensity inside the sample is always less than the intensity at the surface of the material to be ablated. Since it is often necessary to confine ablation and potential damage to the surface of the sample, focusing above the plane of the sample and then adjusting the intensity of the light to the minimum necessary for ablation ensures that no region beneath the surface of the sample will be ablated or damaged.

Our focusing technique is particularly critical when ultrashort (<10 psec) pulsed lasers are utilized for ablation. Since ultrashort pulsed laser ablation is non-thermal, the ablated region is limited to the spatial extent of the focused laser light. Therefore, to eliminate ablation and damage to the underlying substrate, it is essential to ensure that the peak light intensity occurs outside the sample. Our method ensures this. Our technique contrasts significantly with laser ablation in which the objective is to remove large quantities of material without regard to inflicting damage to the underlying substrate. In this case, by focusing the laser beam at or below the surface the laser intensity peaks inside the material (see FIG. 14b). This results in the maximum ablation efficiency, a desirable characteristic when drilling a simple hole without regard to substrate damage.

The following are examples which illustrate the benefit of focusing the laser beam above the surface of the sample to avoid sample damage. In the course of developing a tool to ablate chromium defects on a quartz photomask, we focused a femtosecond pulsed laser beam onto the surface of the chromium. We found that it was difficult to avoid damaging the underlying quartz substrate using this approach, since the normal variation in focus which typically occurred would often cause the laser beam to be focused inside the quartz. When the beam focus occurred in the quartz, the laser intensity was sufficient to damage the quartz rendering the photomask unusable. However, by focusing the laser beam above the chromium surface, we could adjust the laser intensity so that the Cr was ablated while the quartz was unaffected. Similarly, in removing unwanted biological tissue such as a tumor from an organ, focusing the laser beam above the surface of the tumor results in its removal without damaging the underlying tissue. Consider a tumor attached to the retina of the eye. Focusing a pulsed laser at or below the surface of the tumor can result in a maximum laser intensity in the retina rather than the tumor. As the tumor is slowly ablated by the laser beam, the laser intensity at or below the retina will be greater than the laser intensity at the tumor if the laser is focused at or below the surface of the tumor. Focusing above the surface of the tumor ensures that the laser intensity is as small as possible at the retina and decreases with increasing depth into the retina. This minimizes inadvertent damage to the retina.

Figure 2:
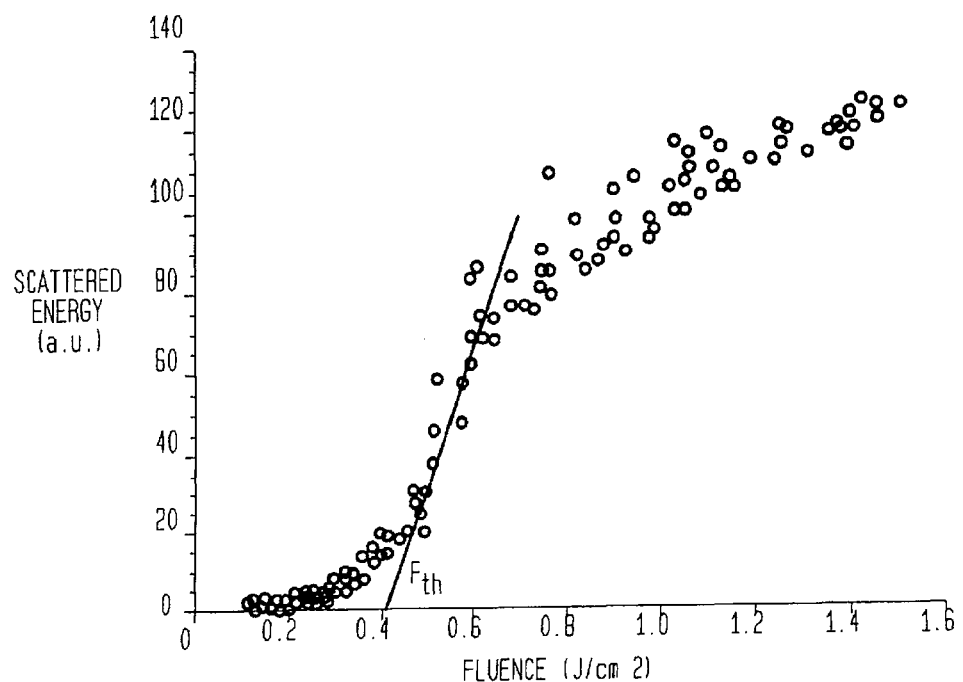
FIG. 2 is a plot of scattered energy versus incident fluence obtained for an opaque (gold) sample using the system in FIG. 1 operated at 150 femtoseconds (fs) pulse duration.
Figure 15:
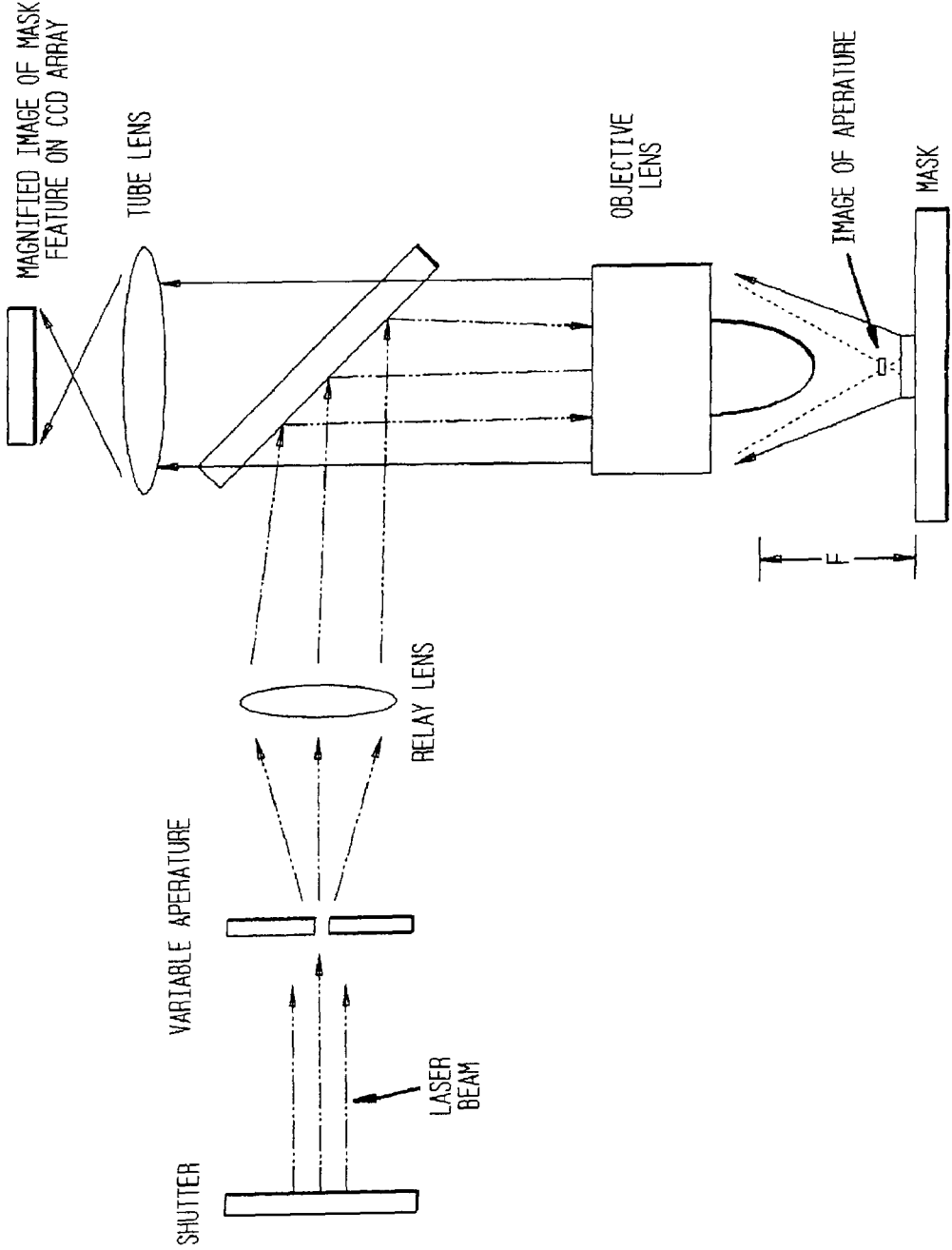
FIG. 15 is an optical system for repairing a photomask. The laser beam illuminates an aperture which is then imaged below the surface of the mask.

There are numerous methods of controlling the focal position of the laser beam which will ensure that the maximum intensity occurs above the surface of the material to be ablated. FIG. 2 shows a schematic diagram of the optical system for repairing chromium defects on a photomask. An objective lens forms an image of the mask on a video camera such as a CCD array. By adjusting the distance (F) between the mask and the objective, the image can be brought into a sharp focus. The optimal distance provides a high quality image of the mask with excellent spatial resolution. This optimal distance can be determined by visually inspecting the sharpness of the image on the CCD array as the distance is varied, using either a computer to perform an analysis of the mask image or manually determining the best focused image. Alternatively, a height sensor can be used to maintain the optimum distance between the mask and the objective lens. The laser beam shown in FIG. 15 illuminates an aperture, which in turn is imaged onto the mask using the relay lens and the mirror. We intentionally adjust the position of the relay lens to ensure that the image of the aperture is focused somewhat above the plane of the mask when the objective lens is adjusted to the optimal imaging distance. Since the objective lens has a large numerical aperture, small variations in the distance between the mask and objective can result in large changes in the effective optical intensity at or below the mask surface. Typically, the uncertainty in the distance F shown in FIG. 15 is comparable to the depth of focus of the optical system. The depth of focus (D) is related to the wavelength of the light (W) and the numerical aperture of the objective lens (NA), and is given approximately by: $D \approx W/(2*(NA)^2)$ We adjust the position of relay lens to form an image of the aperture a distance slightly greater than D above the plane of the mask, with the mask image at best focus. For the mask repair tool we constructed, the numerical aperture is approximately 0.95 and the wavelength of light is 400 nm. Using the method described above, we would typically form an image of the aperture approximately 300 nm above the plane of the mask. This ensures that the peak optical intensity from the laser beam occurs above the mask rather than at or below the surface of the mask, even in cases where the mask image is slightly out of focus (due to the typical uncertainty in determining the optimum focus). The slight defocus in the aperture image at the mask plane has a negligible effect on the spatial resolution of the ablated region.

Figure 16:
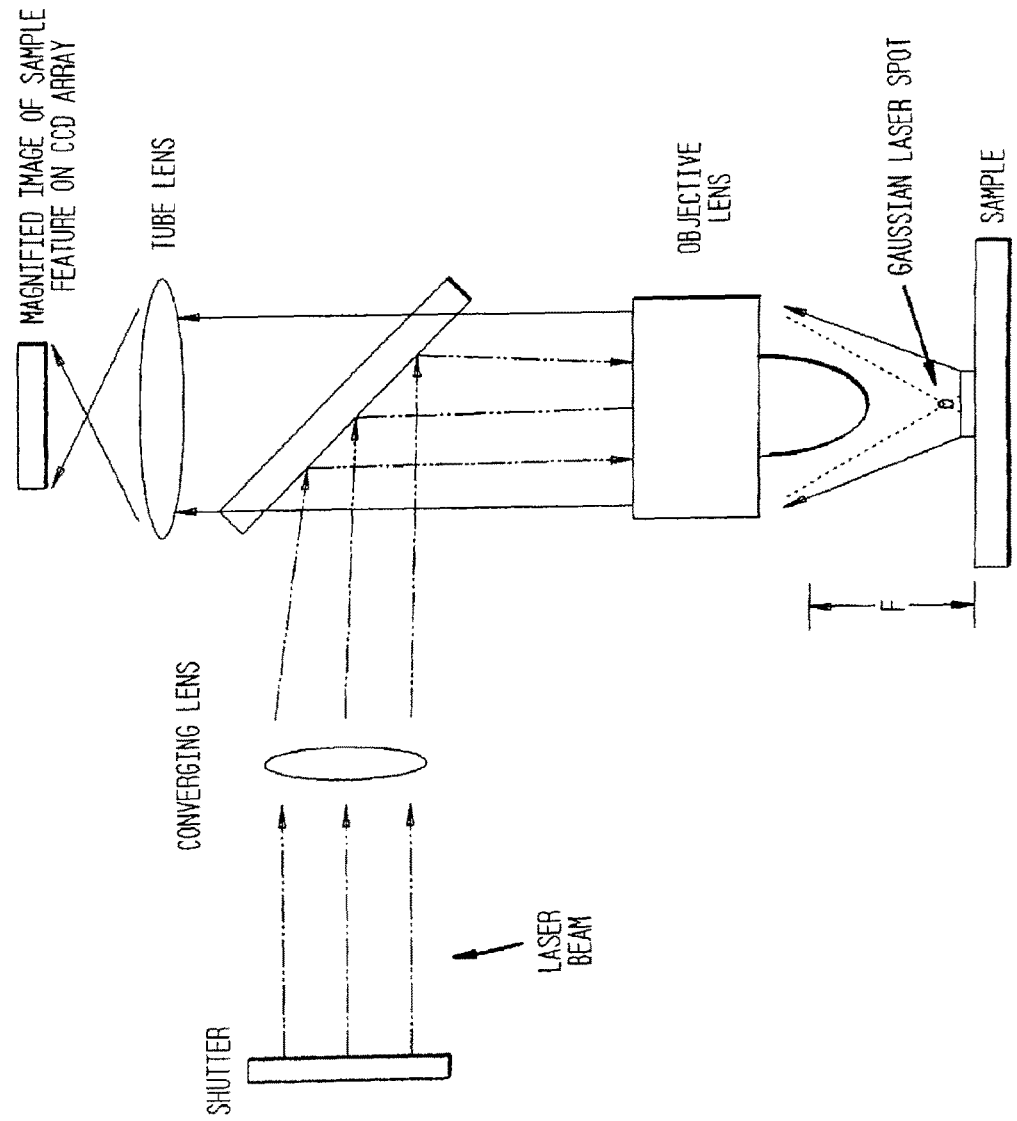
FIG. 16 is a general optical system. A slightly converging laser beam is focused to a gaussian spot slightly above the plane of the mask.

A more general optical approach is shown in FIG. 16. As in the case described above, the distance (F) between the objective lens and the sample is adjusted to bring the image of the sample to the best focus (highest spatial resolution image). However, in this case the laser beam does not illuminate an aperture. Rather, the entire beam enters the objective lens and is focused to a gaussian spot. By adjusting the convergence angle of the laser beam, either through internal adjustments in the laser or through the use of a weak external lens system, the laser beam is brought to a focus slightly above the surface of the sample. The laser intensity is adjusted independently (using filters or a combination of a waveplate and frequency doubling crystal) to a value such that ablation just occurs at the sample surface. Since the peak laser intensity occurs above the surface of the sample rather than inside the sample, the possibility of ablation or damage to the underlying material in the substrate is minimized.

In both cases described above, the focus of the laser beam above the surface of the sample can be maintained by 1) establishing a fixed offset in the relative focus of the sample image and the laser beam, and 2) maintaining the sample at the optimal distance from the objective by monitoring the sample image and/or a height sensor. If a significant depth of material must be removed (e.g. greater than the depth of focus of the optical system), then the distance between the sample and the objective lens can be continuously varied by monitoring the depth of the ablated material and moving either the objective or the sample in the Z direction.

DETAILED DESCRIPTION OF THE PREFERRED EMBODIMENTS

Figure 14A:
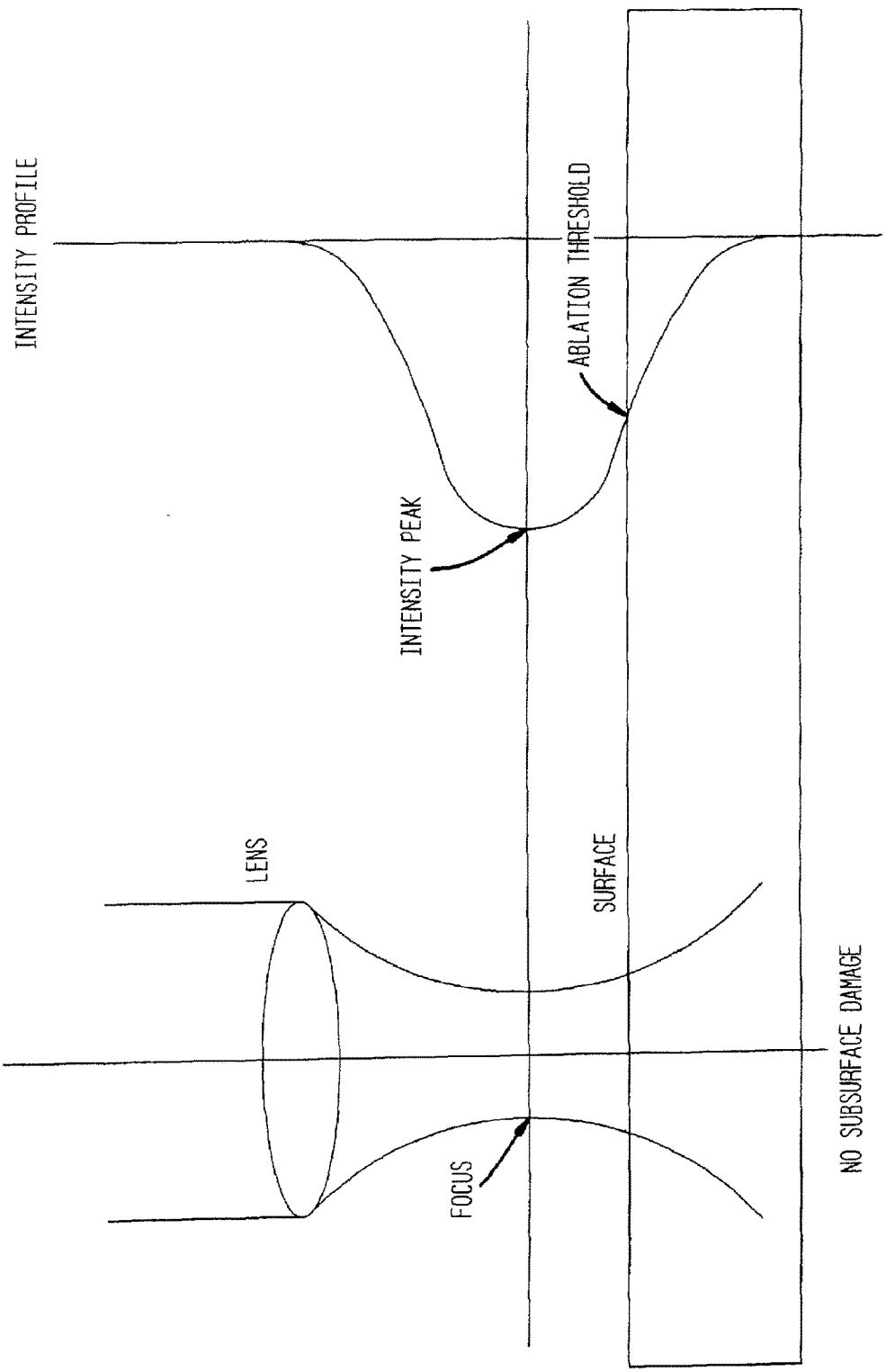
FIG. 14a shows light source focused above the surface to be ablated.

FIG. 14a shows light source focused above the surface of the layer to be ablated.

FIG. 14b shows a light source focused beneath the surface of the layer to be ablated.

FIG. 15 is an optical system for repairing a photomask. The laser beam illuminates an aperture which is then imaged above the surface of the mask.

FIG. 16 is a general optical system. A slightly converging laser beam is focused to a gaussian spot slightly above the plane of the mask.

Referring to FIG. 1 there is shown an apparatus for performing tests to determine the laser induced breakdown threshold as a function of laser pulse width in the nanosecond to femtosecond range using a chirped-pulse amplification (CPA) laser system. The basic configuration of such a CPA system is described in U.S. Pat. No. 5,235,606 which is assigned to the assignee of the present invention and which has inventors in common with this present application. U.S. Pat. No. 5,235,606 is incorporated herein by reference in its entirety.

Chirped-pulse amplification systems have been described by Jeffrey Squier and Gerard Mourou, two of the joint inventors in the present application, in a publication entitled Laser Focus World published by Pennwell in June of 1992. It is described that CPA systems can be roughly divided into four categories. The first includes the high energy low repetition systems such as ND glass lasers with outputs of several joules but they may fire less than 1 shot per minute. A second category are lasers that have an output of approximately 1 joule and repetition rates from 1 to 20 hertz. The third group consists of millijoule level lasers that operate at rates ranging from 1 to 10 kilohertz. A fourth group of lasers operates at 250 to 350 kilohertz and produces a 1 to 2 microjoules per pulse. In U.S. Pat. No. 5,235,606 several solid state amplifying materials are identified and the invention of U.S. Pat. No. 5,235,606 is illustrated using the Alexandrite. The examples below use Ti: Sapphire and generally follow the basic process of U.S. Pat. No. 5,235,606 with some variations as described below.

The illustrative examples described below generally pertain to pulse energies less than a microjoule and often in the nanojoule range with pulse duration in the range of hundreds of picoseconds or less and the frequency on the order of 1 kilohertz. But these examples are merely illustrative and the invention is not limited thereby.

In a basic scheme for CPA, first a short pulse is generated. Ideally the pulse from the oscillator is sufficiently short so that further pulse compression is not necessary. After the pulse is produced it is stretched by a grating pair arranged to provide positive group velocity dispersion. The amount the pulse is stretched depends on the amount of amplification. Below a millijoule, tens of picoseconds are usually sufficient. A first stage of amplification typically takes place in either a regenerative or a multipass amplifier. In one configuration this consists of an optical resonator that contains the gain media, a Pockels cell, and a thin film polarizer. After the regenerative amplification stage the pulse can either be recompressed or further amplified. The compressor consists of a grating or grating pair arranged to provide negative group velocity dispersion. Gratings are used in the compressor to correspond to those in the stretching stage. More particulars of a typical system are described in U.S. Pat. No. 5,235,606, previously incorporated herein by reference.

An important aspect of the invention is the development of a characteristic curve of fluence breakdown threshold Fth as a function of laser pulse width specific to a material. Then identify on such curve, the point at which there is an abrupt, or distinct and rapid change or at least a discernable change in slope characteristic of the material. In general it is more desirable to operate past this point because of the more precise control of the laser induced breakdown (LIB) or ablation threshold.

EXAMPLE 1

Opaque Material

FIG. 1 shows an experimental setup for determining threshold fluence by determining scattered energy versus incident fluence and by determining threshold fluence versus pulse width. The system includes means for generating a pulsed laser beam as described earlier, and means, typically a lens, for collecting emission from the target to a photomultiplier tube. Change of transmission through a transparent sample is measured with an energy meter.

Figure 3:
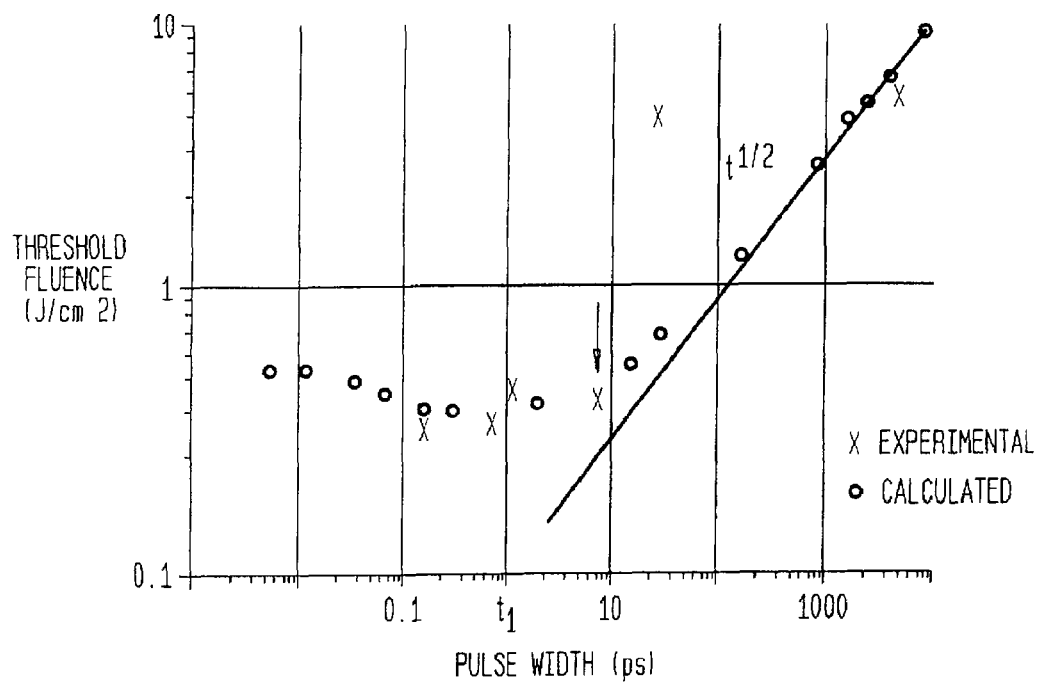
FIG. 3 is a plot of calculated and experimental values of threshold fluence versus pulse width for gold, with experimental values obtained for the gold sample using the system of FIG. 1 operated at 800 nm wavelength. The arrow shows the point on the plot where the Fth proportional to T½ no longer applies, as this relationship only holds for pulse widths down to a certain level as shown by the solid line.

FIG. 2 shows a plot of data obtained from an absorbing medium which is gold using 150 fs pulse and FIG. 3 shows threshold fluence pulse width. The arrow in FIG. 3 identifies the point at which the relationship between the threshold fluence and pulse width varies dramatically.

Figure 4:
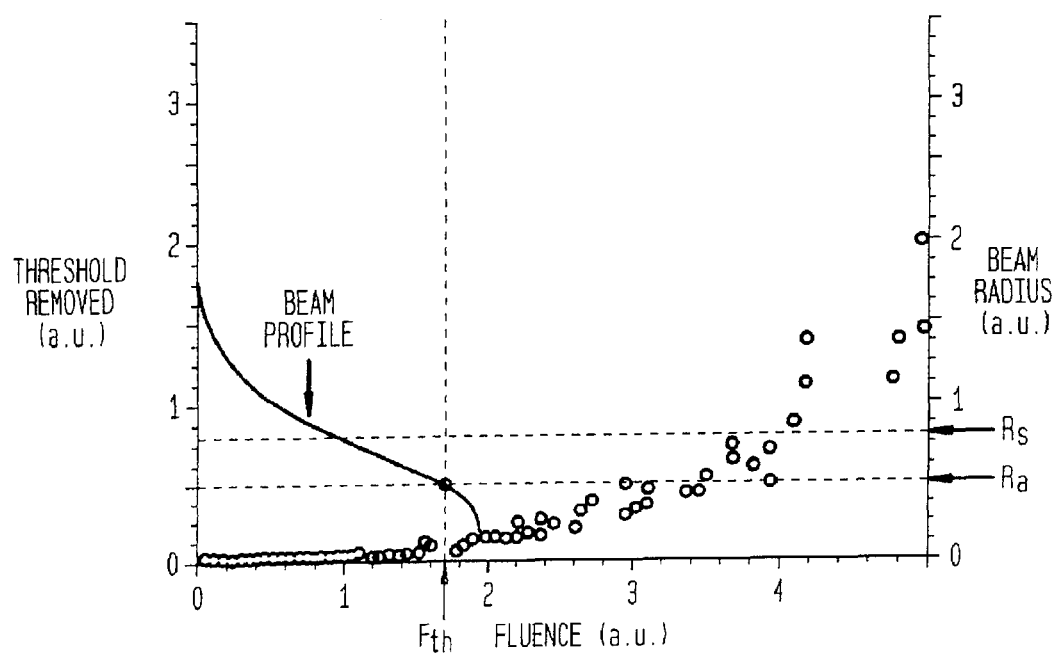
FIG. 4 is a graphical representation of sub-spot size ablation/machining in gold based on arbitrary units and showing Fth the threshold fluence needed to initiate material removal; Rs the spot size of the incident beam and Ra the radius of the ablated hole in the x-y plane.
Figure 5:
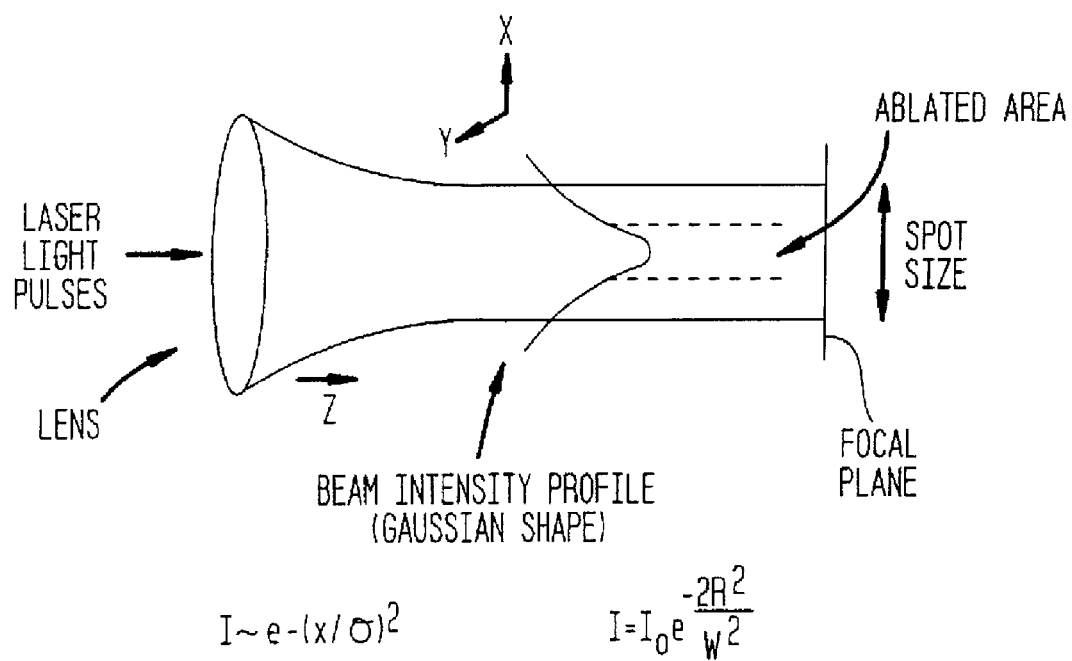
FIG. 5 is a schematic illustration of a beam intensity profile showing that for laser micro-machining with ultrafast pulse according to the invention, only the peak of the beam intensity profile exceeds the threshold intensity for ablation/ machining.

In experimental conditions with wavelength of 800 nm and 200 fs pulses on gold (FIG. 3), the absorption depth is 275 A with a diffusion of 50 A. In the case of nanosecond pulses the diffusion length, which is on the order of 10 urn (micron) in diameter, is much longer than the absorption depth, resulting in thermal diffusion being the limiting factor in feature size resolution. Empirical evidence for the existence of these two regimes is as exhibited in FIG. 3. Here both experimental and theoretical ablation thresholds are plotted as a function of pulse width. An arrow at approximately 7 picoseconds pulse width (designated herein as T or .tau.p) delineates the point (or region closely bounding that point) at which the thermal diffusion length (lth) is equal to the absorption depth (I/a). It is clear that for a smaller size spot a shorter (smaller) pulse is necessary. For spot size on the order of 1000 .ANG. or less, pulse width on the order of 100 femtoseconds or less will be needed. It is clear from the figure that this is the point at which the ablation threshold transitions from a slowly varying or nearly constant value as a function of pulse width to one that is dramatically dependent on pulse time. This result is surprising. It has been that the electron thermalization time for laser deposited energy in gold is on the order o.English Pound. or less than, 500 fs and the electron-lattice interaction time is 1 ps. The consequences of this for ultrafast laser pulses is that the energy is contained within the beam spot. In fact for energies at or near the threshold for ablation, the spatial profile of the laser beam will determine the size and shape of the region being ablated (FIGS. 4 and 5).

Additional experiments were performed to measure the amount of recombination light produced as a function of the fluence impinging on a gold film. The technique involved is based upon the experimental setup previously described. A basic assumption is that the intensity of the light is proportional to the amount of material ablated. In FIG. 4, the material removed is plotted as a function of fluence. A well defined threshold fluence is observed at which material removal is initiated. By having only a small fraction of the gaussian beam where the fluence is greater than the threshold, the ablated region can be restricted to this small area. In FIG. 4, Ra is the radial position on the beam where the fluence is at threshold. Ablation, then, occurs only within a radius Ra. It is evident that by properly choosing the incident fluence, the ablated spot or hole can in principle be smaller than the spot size, Rs. This concept is shown schematically in FIG. 5. Although the data for a 150 fs pulse is shown in FIG. 4, this threshold behavior is exhibited in a wide range of pulse widths. However, sub spot size ablation is not possible in the longer pulse regimes, due to the dominance of thermal diffusion as will be described below. Additional experiments on opaque materials used a 800 nm Ti:Sapphire oscillator whose pulses were stretched by a grating pair, amplified in a regenerative amplifier operating at 1 kHz, and finally recompressed by another grating pair. Pulse widths from 7 ns to 100 fs were obtained. The beam was focused with a 10* objective, implying a theoretical spot size of 3.0 urn in diameter. A SEM photo-micrograph of ablated holes obtained in a silver film on glass, using a pulse width of 200 fs and a pulse energy of 30 nJ (fluence of 0.4 J/cm2) produced two holes of diameter approximately 0.3 urn in diameter. Similar results have been obtained in aluminum.

These results suggest that by, producing a smaller spot size which is a function of numerical aperture and wavelength, even smaller holes can be machined. We have demonstrated the ability to generate the fourth harmonic (200 nm) using a nonlinear crystal. Thus by using a stronger objective lens along with the 200 nm light, holes with diameters of 200 angstroms could in principle be formed.

These examples show that by using femtosecond pulses the spatial resolution of the ablation/machining process can be considerably less than the wavelength of the laser radiation used to produce it. The ablated holes have an area or diameter less than the area or diameter of the spot size. In the special case of diffraction limited spot size, the ablated hole has a size (diameter) less than the fundamental wavelength size. We have produced laser ablated holes with diameters less than the spot diameter and with diameters 10% or less of the laser beam spot size. For ultrafast pulses in metals the thermal diffusion length, $lth=(Dt)^{1/2}$ (where D is the thermal difflisivity and t the pulse time), is significantly smaller than the absorption depth (l/a), where a is the absorption coefficient for the radiation.

Those skilled in the art will understand that the basic method of the invention may be utilized in alternative embodiments depending on desired configurations of the induced breakdown. Examples include, but are not limited to using a mask in the beam path, varying spot size, adjusting focus position by moving the lens, adjusting laser cavity design, Fourier Transform (FT) shaping, using a laser operating other than TEMoo, and adjusting the Rayleigh range, the depth of focus or beam waist.

Figure 6A:
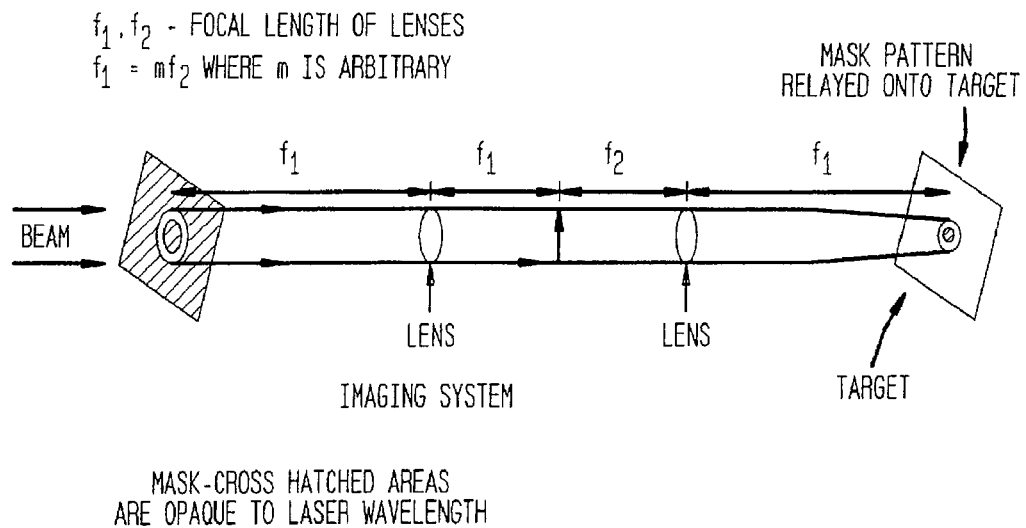
FIGS. 6A and B are schematic illustrations of a beam showing the placement of a disk-shaped mask in the beam path.
Figure 6B:
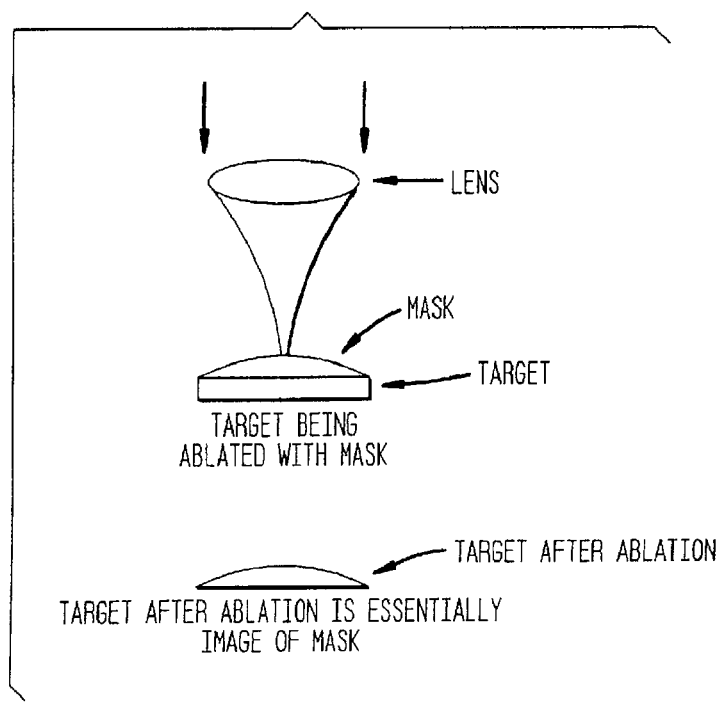

The use of a mask is illustrated in FIGS. 6A and B. The basic method consists of placing a mask in the beam path or on the target itself. If is desired to block a portion of the beam, the mask should be made of an opaque material and be suspended in the beam path (FIG. 6A), the mask may be placed on the target and be absorptive so as to contour the target to the shape of the mask (FIG. 6B).

The varying spot size is accomplished by varying the laster f7#, i.e., varying the focal length of the lens or input beam size to the lens as adjustable diaphragm, in other than the TEMoo mode means that higher order transverse modes could be used. This affects the beam and material as follows: the beam need not be circular or gaussian in intensity. The material will be ablated corresponding to the beam shape.

The Rayleigh range (Z axis) may be adjusted by varying the beam diameter, where the focal plane is in the x-y axis.

EXAMPLE 2

Transparent Material

A series of tests were performed on an SiO2 (glass) sample to determine the laser induced breakdown (LIB) threshold as a function of pulse width between 150 fs-7 ns, using a CPA laser system. The short pulse laser used was a 10 Hz Ti: Sapphire oscillator amplifier system based on the CPA technique. The laser pulse was focused by an f=25 cm lens inside the SiO2 sample. The Rayleigh length of the beam is .about.2 mm. The focused spot size was measured in-situ by a microscope objective lens. The measured spot size FWHM (full at half max) was 26 urn in diameter in a gaussian mode. The fused silica samples were made from Corning 7940, with a thickness of 0.15 mm. They were optically polished on both sides with a scratch/dig of 20-10. Each sample was cleaned by methanol before the. Thin samples were used in order to avoid the complications of self-focusing of the laser pulses in the bulk. The SiO2 sample mounted on a computer controlled motorized X-Y translation stage. Each location on the sample was illuminated by the laser only once.

Figure 7:
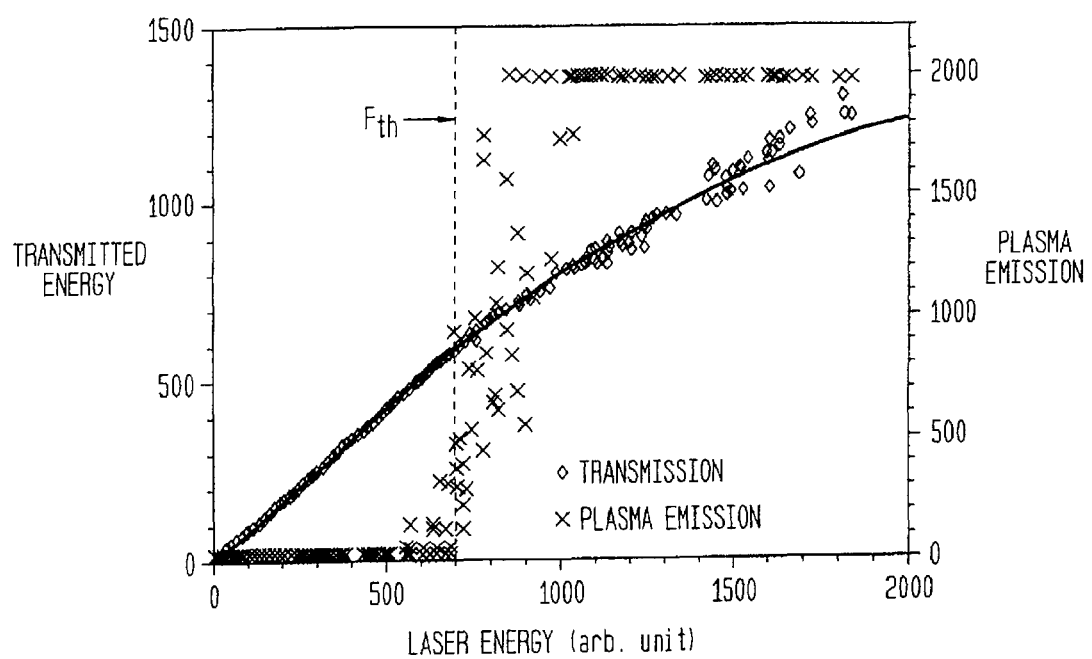
FIG. 7 is a plot of scattered plasma emission and transmitted laser pulse as a function of incident laser pulse energy for a transparent glass sample, SiO2.

Two diagnostics were used to determine the breakdown threshold Fth. First, the plasma emission from the focal region was collected by a lens to a photomultiplier tube with appropriate filters. Second, the change of transmission through the sample was measured with an energy meter. (See FIG. 1) Visual inspection was performed to confirm the breakdown at a nanosecond pulse duration. FIG. 7 shows typical plasma emission and transmitted light signal versus incident laser energy plots, at a laser pulse width of .tau.p=300 fs. It is worth noting that the transmission changed slowly at around Fth. This can be explained by the temporal and spatial behavior of the breakdown with ultrashort pulses. Due to the spatial variation of the intensity, the breakdown will reach threshold at the center of the focus, and because of the short pulse duration, the generated plasma will stay localized. The decrease in transmitted light is due to the reflection, scattering, and absorption by the plasma. By assuming a gaussian profile in both time and space for the laser intensity, and further assuming that the avalanche takes the entire pulse duration to reach threshold, one can show that the transmitted laser energy Ut as a function of the input energy U is given by Ut=kU, U<=Uth Ut=kUth[1+ln(U/Uth)], U>Uth where k is the linear transmission coefficient. The solid curve in FIG. 7 is plotted using Eq. (1), with Uth as a fitting parameter. In contrast, breakdown caused by nanosecond laser pulses cuts off the transmitted beam near the peak of the pulses, indicating a different temporal and spatial behavior.

Figure 8:
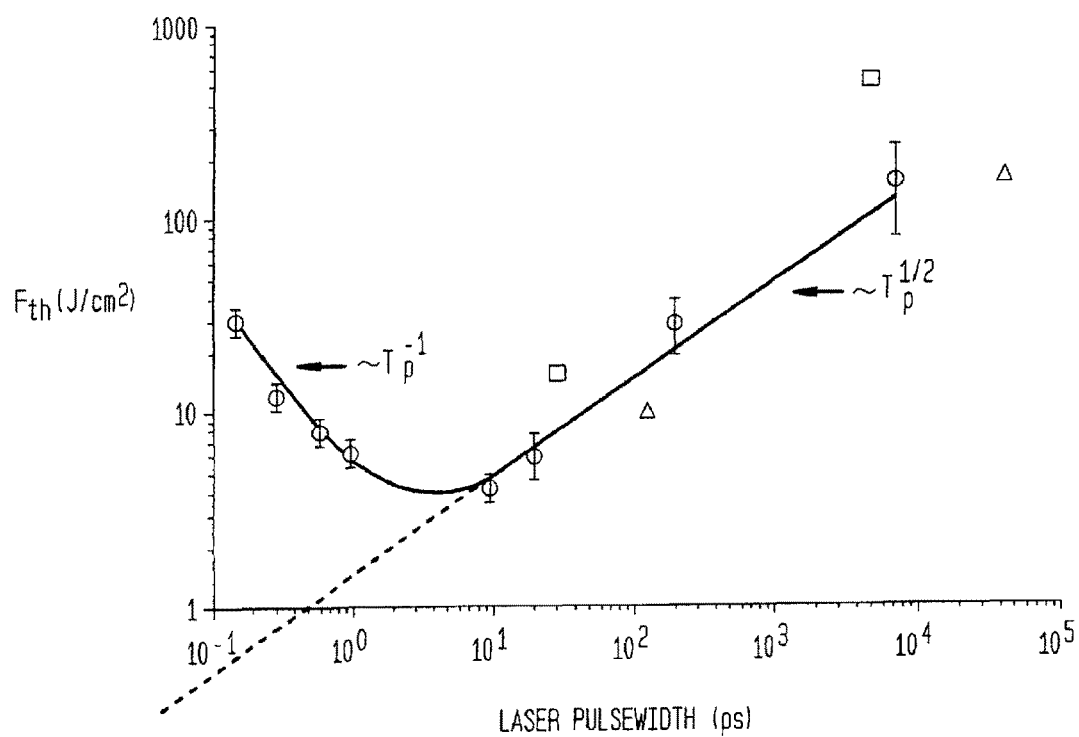
FIG. 8 is a plot of fluence threshold (Fth) versus pulse width (T) for the transparent glass sample of FIG. 7 showing that Fth varying with T½ only holds for pulse widths down to a certain level as shown by the solid line. Previous work of others is shown in the long pulse width regime (Squares, Smith Optical Eng 17, 1978 and Triangles, Stokowski, NBS Spec Bui 541, 1978).

FIG. 8 shows the fluence breakdown threshold Fth as a function of laser pulse width. From 7 ns to about 10 ps, the breakdown threshold the scaling in the relatively long pulse width regime (triangles and squares) are also shown as a comparison—it can be seen that the present data is consistent with earlier work only in the higher pulse width portion of the curve. When the pulse width becomes shorter than a few picoseconds, the threshold starts to increase. As noted earlier with respect to opaque material (metal), this increased precision at shorter pulse widths is surprising. A large increase in damage threshold accuracy is observed, consistent with the multiphoton avalanche breakdown theory. (See FIGS. 8 and 9.) It is possible to make features smaller than spot size in the x-y focal plane and smaller than the Rayleigh range (depth of focus) in the longitudinal direction or Z axis. These elements are essential to making features smaller than spot size or Rayleigh range.

EXAMPLE 3

Tissue

A series of experiments was performed to determine the breakdown threshold of cornea as a function of laser pulse width between 150 ns, using a CPA laser system. As noted earlier, in this CPA laser system, laser pulse width can be varied while all other experimental parameters (spot size, wavelength, energy, etc.) remain unchanged. The laser was focused to a spot size (FWHM) of 26 ^m in diameter. The plasma emission was recorded as a function of pulse energy in order to determine the tissue damage threshold. Histologic damage was also assessed.

Figure 9:
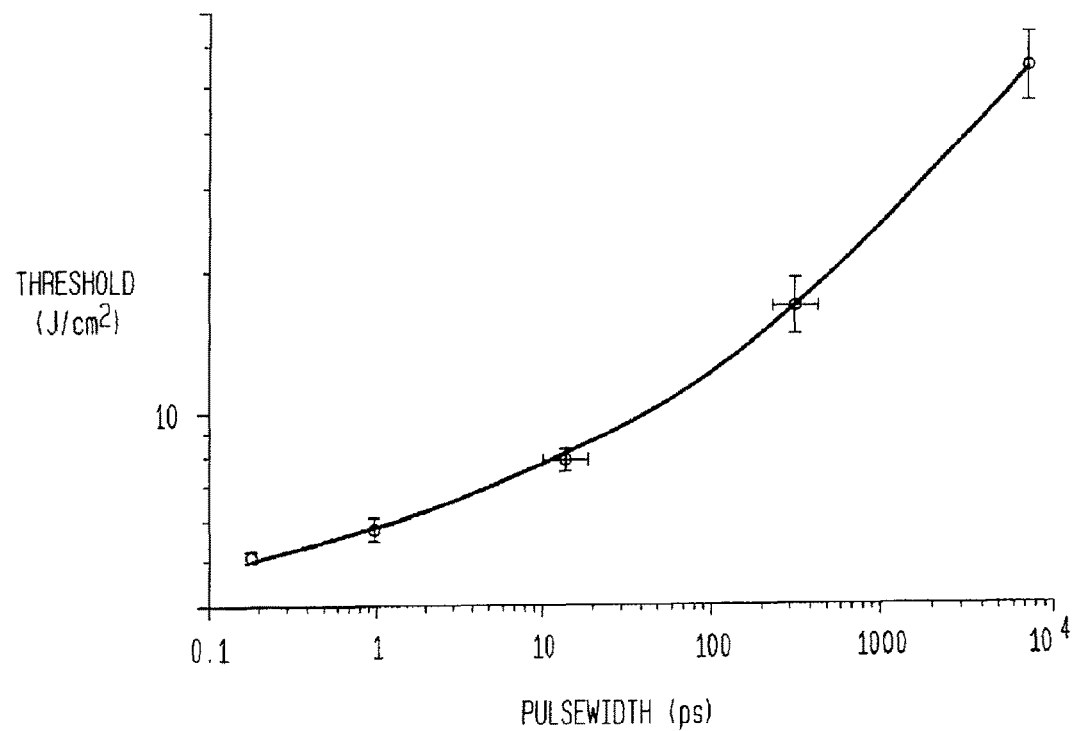
FIG. 9 is a plot of fluence threshold versus pulse width for corneal tissue, again showing that the proportionality between Fth and pulse width follows the T½ relationship only for pulse widths which are relatively long.
Figure 10:
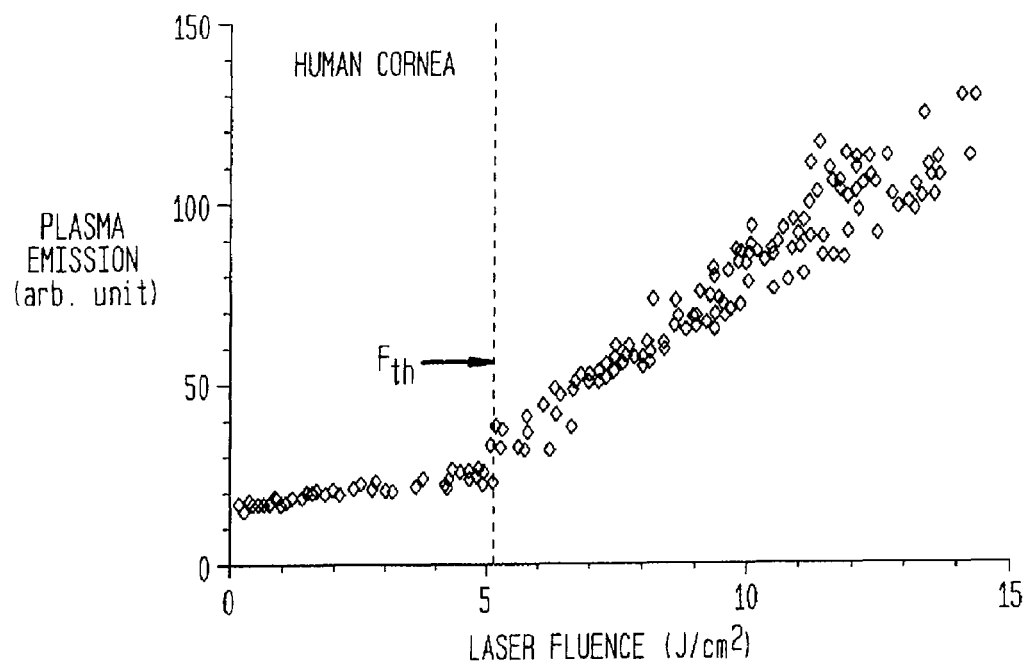
FIGS. 10 and 11 are plots of plasma emission versus laser fluence showing that at 170 (FIG. 10) pulse width the Fth is very clearly defined compared to 7 nm (FIG. 11) pulse width where it is very unclear.
Figure 11:
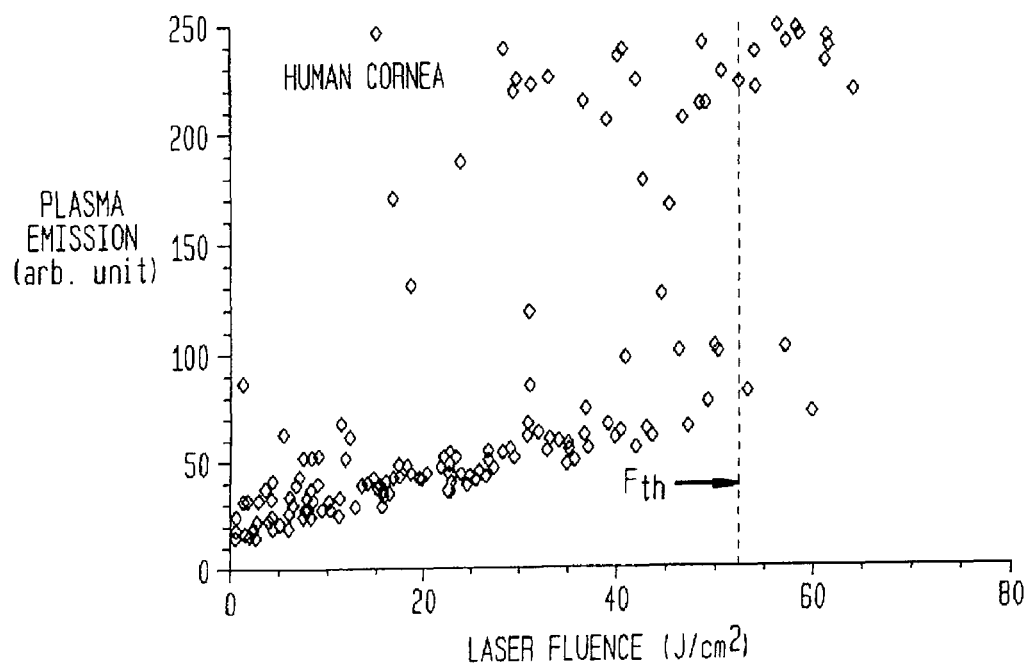

Breakdown thresholds calculated from plasma emission data revealed deviations from the scaling law, Fth .alpha. T½, as in the case of and glass. As shown in FIG. 9, the scaling law of the fluence threshold is true to about 10 ps, and fail when the pulse shortens to less than a few picoseconds. As shown in FIGS. 10 and 11, the ablation or LIB threshold varies dramatically at high (long) pulse width. It is very precise at short pulse width. These results were obtained at 770 nm wavelengths. The standard deviation of breakdown threshold measurements decreased markedly with shorter pulses. Analysis also revealed less adjacent histological damage with pulses less than 10 ps.

The breakdown threshold for ultrashort pulses (<10 ps) is less than longer pulses and has smaller standard deviations. Reduced adjacent histological damage to tissue results from the ultrashort laser pulses.

In summary, it has been demonstrated that sub-wavelength holes can be machined into metal surfaces using femtosecond laser pulses. The effect is physically understood in terms of the thermal diffusion length, over the time period of the pulse deposition, being less than the absorption depth of the incident radiation. The interpretation is further based on the hole diameter being determined by the lateral gaussian distribution of the pulse in relation to the threshold for vaporization and ablation.

Laser induced optical breakdown dielectrics consists of three general steps: free electron generation and multiplication, plasma heating and material deformation or breakdown. Avalanche ionization and multiphoton ionization are the two processes responsible for the breakdown. The laser induced breakdown threshold in dielectric material depends on the pulse width of the laser pulses. An empirical scaling law of the fluence breakdown threshold as a function of the pulse width is given by Fth .alpha. .sqroot..tau.p, or alternatively, the intensity breakdown threshold, Ith=Fth/.tau.p. Although this scaling law applies in the pulse width regime from nanosecond to tens of picoseconds, the invention takes advantage of the heretofore unknown regime where breakdown threshold does not follow the scaling law when suitably short laser pulses are used, such as shorter than 7 picoseconds for gold and 10 picoseconds for SiO2.

While not wishing to be held to any particular theory, it is thought that the ionization process of a solid dielectric illuminated by an intense laser pulse can be described by the general equation dne(t)/dt=.eta.(E)ne(t)+(dne(t)/dt)PI−(dne(t)/dt)loss where ne(t) is the free electron (plasma) density, .eta.(E) is the avalanche coefficient, and E is the electric field strength. The second term on the right hand side is the photoionization contribution, and the third term is the loss due to electron diffusion, recombination, etc. When the pulse width is in the picosecond regime, the loss of the electron is negligible during the duration of the short pulse.

Photoionization contribution can be estimated by the tunneling rate. For short pulses, E-108 V/cm, the tunneling rate is estimated to be w.about.4.times.109 sec-1, which is small compared to that of avalanche, which is derived below. However, photoionization can provide the initial electrons needed for the avalanche processes at short pulse widths. For example, the data shows at 1 ps, the rms field threshold is about 5><107 V/cm. The field will reach a value of 3.5.times.107 V/cm (rms) at 0.5 ps before the peak of the pulse, and w.about.100 sec-1. During a DELTA.t.about.100 fs period the electron density can reach ne.about.nt [1-exp (−w.DELTA.t)].about.1011 cm-3, where nt-1022 is the total initial valence band electron density.

Neglecting the last two terms there is the case of an electron avalanche process, with impact ionization by primary electrons driven by the laser field. The electron density is then given by ne (t)=no x exp(n(E)t), where no is the initial free electron density. These initial electrons may be generated through thermal ionization of shallow traps or photoionization. When assisted by photoionization at short pulse regime, the breakdown is more statistical. According to the condition that breakdown occurs when the electron density exceeds nth .congruent. 1018 cm-3 and an initial density of no congruent. 1010 cm-3, the breakdown condition is then given by .eta..tau.p congruent. 18. For the experiment, it is more appropriate to use nth .congruent. 1.6.times.1021 cm-3, the plasma critical density, hence the threshold is reached when eta.tau.p .congruent.30. There is some arbitrariness in the definition of plasma density relating to the breakdown threshold. However, the particular choice of plasma density does not change the dependence of threshold as function of pulse duration (the scaling law).

In the experiment, the applied electric field is on the order of a few tens of MY/cm and higher. Under such a high field, the electrons have an average energy of .about.5 eV, and the electron collision time is less than 0.4 fs for electrons with energy U.gtoreq.gt;=5-6 eV. Electrons will make more than one collision during one period of the electric oscillation. Hence the electric field is essentially a dc field to those high energy electrons. The breakdown field at optical frequencies has been shown to correspond to dc breakdown field by the relationship Erm.kappa.th (w)=Edcth (1+w2 .tau.2)½, where w is the optical frequency and .tau. is the collision time.

In dc breakdown, the ionization rate per unit length, .alpha., is used to describe the avalanche process, with .eta.=.alpha.(E)vdrift, where vdrift is the drift velocity of electrons. When the electric field is as high as a few MV/cm, the drift velocity of free electrons is saturated and independent of the laser electric field, vdrift .congruent.2><107 cm/s.

The ionization rate per unit length of an electron is just eE/Ui times the probability, P(E), that the electron has an energy .gtoreq.=Ui, or .alpha.(E)=(eE/Ui)P(E). Denoting EkT,E p, and Ei as threshold fields for electrons to overcome the decelerating effects of thermal, phonon, and ionization scattering, respectively. Then the electric field is negligible, EkT, so the distribution is essentially thermal, P(E) is simply exp(−Ui/kT). It has been suggested: P(E).about.exp(−const/E) for EkT p; P(E).about.exp(−const/E2) at higher fields (E>Ep). Combining the three cases the expression that satisfies both low and high field limits: .alpha.(E)=(eE/Ui) exp(−Ei/(E(1+E/Ep)+EKT).

This leads to Fth .alpha. E2 .tau.p.about.l/.tau.p, i.e., the fluence threshold will increase for ultrashort laser pulses when E>.sqroot.Ep Ei is satisfied.

Figure 12:
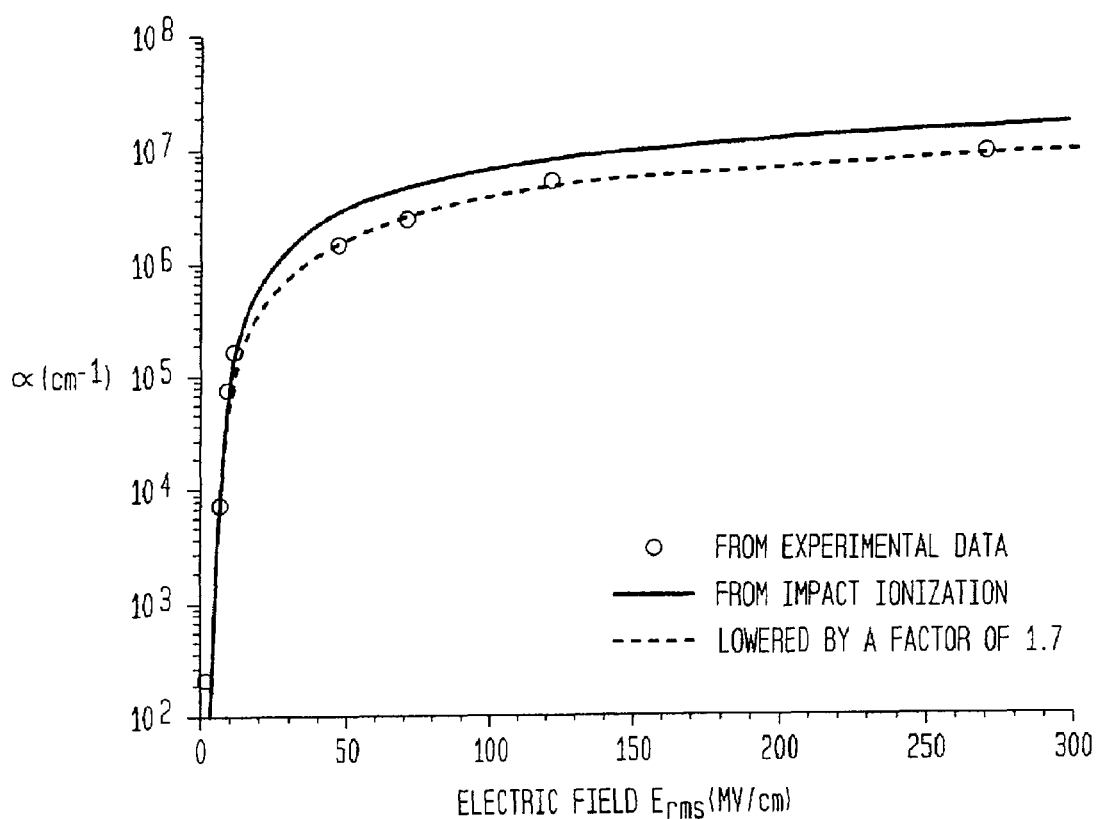
FIG. 12 is a plot of impact ionization rate per unit distance determined by experiment and theoretical calculation.

FIG. 12 is a plot of .alpha. as a function of the electric field, E. From experimental data, calculated according to .eta..tau.p=30 and eta.=avdrift. The solid curve is calculated from the above equation, using Ei=30 MV/cm, Ep=3.2 MV/cm, and EkT=0.01 MV/cm.

These parameters are calculated from U=eEl, where U is the appropriate thermal, phonon, and ionization energy, and l is the correspondent energy relation length (lkT=lp .about.5 .ANG., the atomic spacing, and li .congruent.30 .ANG.). It shows the same saturation as the experimental data. The dashed line is corrected by a factor of 1.7, which results in an excellent fit with the experimental data. This factor of 1.7 is of relatively minor importance, as it can be due to a systematic correction, or because breakdown occurred on the surface first, which could have a lower threshold. The uncertainty of the saturation value of vdrift also can be a factor. The most important aspect is that the shape (slope) of the curve given by the equation provides excellent agreement with the experimental data. Thus, the mechanism of laser induced breakdown in fused silica (Example 2), using pulses as short as 150 fs and wavelength at 780 nm, is likely still dominated by the avalanche process.

Figure 13A:
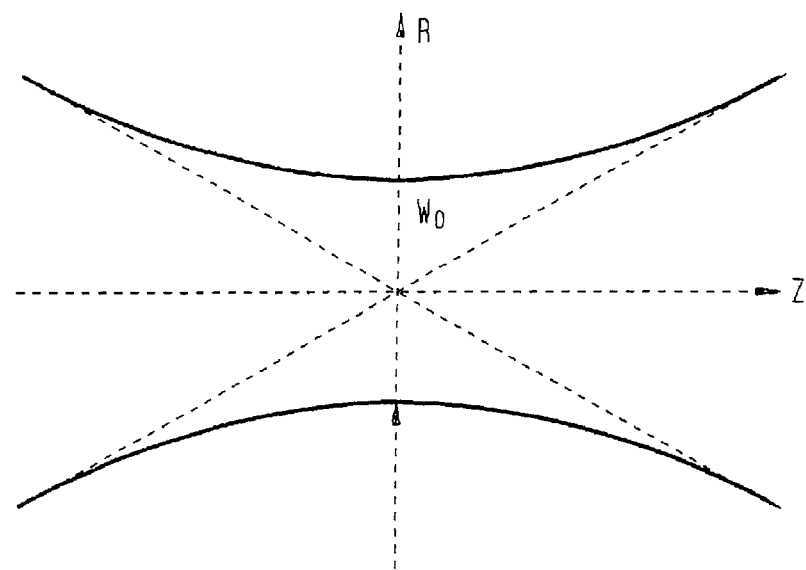
FIGS. 13A and B are schematic illustrations of beam profile along the longitudinal Z axis and sharing precise control of damage-dimension along the Z axis.
Figure 13B:
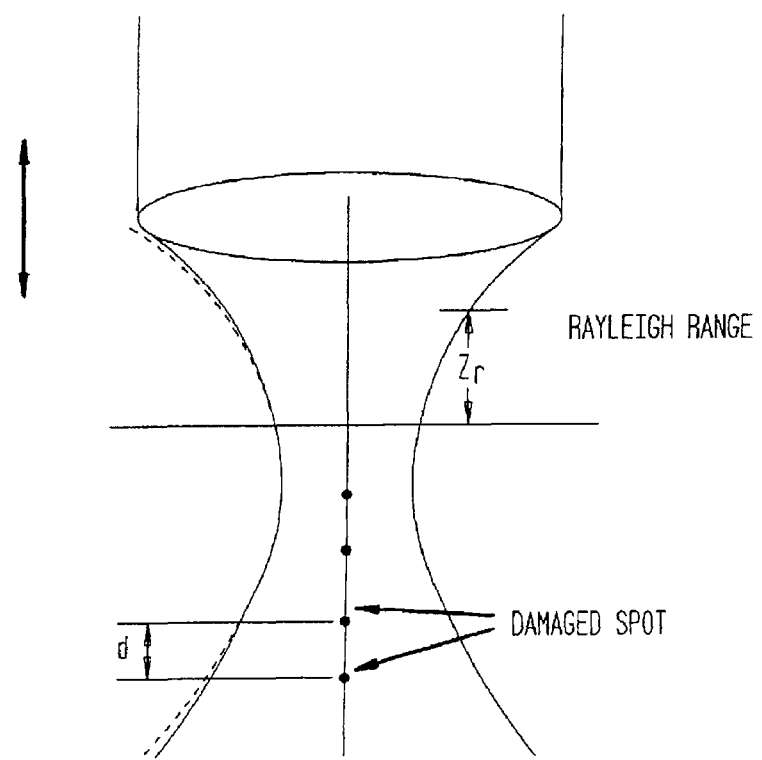

Opaque and transparent materials have common characteristics in the curves of FIGS. 3, 8, and 9 each begins with Fth versus T½ behavior but then distinct change from that behavior is evident. From the point of deviation, each curve is not necessarily the same since the materials differ. The physical characteristics of each material differ requiring a material specific analysis. In the case of SiO2 FIG. 8) the energy deposition mechanism is by dielectric breakdown. The optical radiation is releasing electrons by multiphoton ionization (M PI) that are tightly bound and then accelerating them to higher energies by high field of the laser. It is thought that only a small amount of relatively high energy electrons exist prior to the laser action. The electrons in turn collide with other bound electrons and release them in the avalanching process. In the case of metal, free electrons are available and instantly absorbing and redistributing energy. For any material, as the pulses get shorter laser induced breakdown (LIB) or ablation occurs only in the area where the laser intensity exceeds LIB or ablation threshold. There is essentially insufficient time for the surrounding area to react thermally. As pulses get shorter, vapor from the ablated material comes off after the deposition of the pulse, rather than during deposition, because the pulse duration is so short. In summary, by the method of the invention, laser induced breakdown of a material causes thermal-physical changes through ionization, free electron multiplication, dielectric breakdown, plasma formation, other thermal-physical changes in state, such as melting and vaporization, leading to an irreversible change in the material. It was also observed that the laser intensity also varies along the propagation axis (FIG. 13). The beam intensity as a function of R and Z expressed as: I((Z,R)=Io/(1+Z/ZR)2.multidot.exp(−2R2AV2z) where ZR is the Rayleigh range and is equal to [Figure] Wo is the beam size at the waist (Z=0).

We can see that the highest value of the field is at Z=R=0 at the center of the waist. If the threshold is precisely defined it is possible to damage the material precisely at the waist and have a damaged volume representing only a fraction of the waist in the R direction or in the Z direction. It is very important to control precisely the damage threshold or the laser intensity fluctuation.

For example, if the damage threshold or the laser fluctuations known within 10% that means that on the axis (R=0) I(0,Z)/Io=1/(l=(Z/ZR)2=0.9 damaged volume can be produced at a distance ZR/3 where ZR again is the Rayleigh range. For a beam waist of Wo=.lambda., then Figure] and the d distance between hole can [Figure] as shown in FIG. 13.

The maximum intensity is exactly at the center of the beam waist (Z=0, R=0). For a sharp threshold it is possible to damage transparent, dielectric material in a small volume centered around the origin point (Z=0, R=0). The damage would be much smaller than the beam waist in the R direction. Small cavities, holes, or damage can have dimensions smaller than the Rayleigh range (ZR) in the volume of the transparent, dielectric material. In another variation, the lens can be moved to increase the size of the hole or cavity in the Z dimension. In this case, the focal point is essentially moved along the Z axis to increase the longitudinal dimension of the hole or cavity. These features are important to the applications described above and to related applications such as micro machining, integrated circuit manufacture, and encoding data in data storage media.

Advantageously, the invention identifies the regime where breakdown threshold fluence does not follow the scaling law and makes use of such regime to provide greater precision of laser induced breakdown, and to induce breakdown in a preselected pattern in a material or on a material. The invention makes it possible to operate the laser where the breakdown or ablation threshold becomes essentially accurate. The accuracy can be clearly seen by the I-bars along the curves of FIGS. 8 and 9. The I-bars consistently show lesser deviation and correspondingly greater accuracy in the regime at or below the predetermined pulse width.

Figure 32:
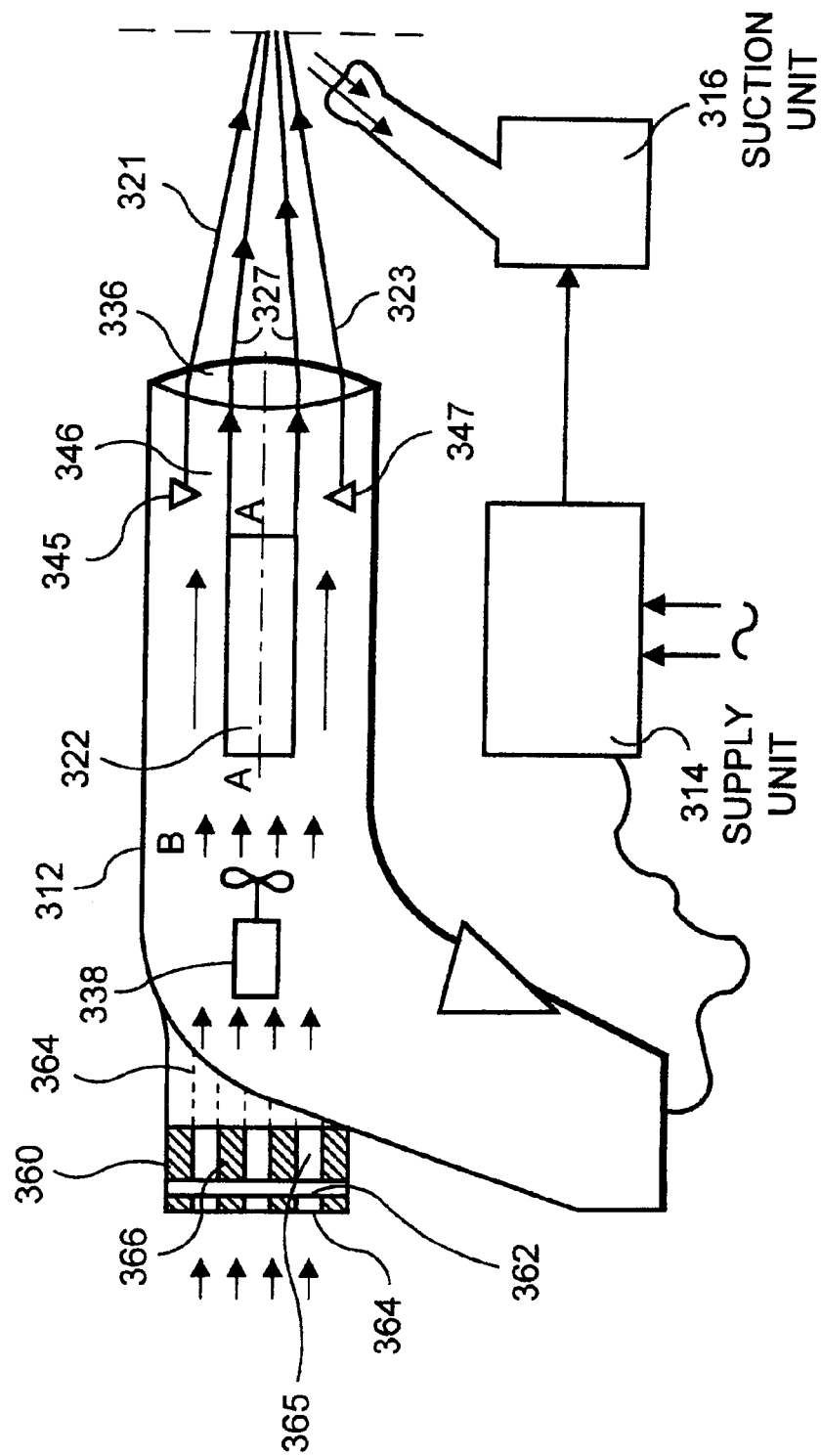
FIG. 32. shows a cooling arrangement of the invention.

Referring to the drawings, in which there is shown in FIG. 17 an apparatus 10 for performing of a laser surgery. The apparatus 10 consists of the following main units: a compact surgical laser instrument or a handpiece 12, a power supply unit 14 producing high-voltage potential pulses with tunable parameters, a suction unit or suction apparatus 16 for suction of disintegrated skin products resulted from application of an operating laser beam to a targeted area and a control unit 18. The handpiece formed with a housing 20 is adapted to be conveniently held in the hands of an operator. It is best illustrated in FIG. 32 that a laser cavity 22 is provided within the interior area of the housing 20. An operating laser assembly 24 is situated within the laser cavity and consists of an active laser element or rod 26, an exciting arrangement 28 and an optical resonator 30. The exciting arrangement which is adapted for exciting of the operating laser element can be any conventional exciting device such as, for example, a flash lamp or a diode laser.

The optical resonator 30 includes a mirror 32 having high reflective capabilities and positioned rearwardly of the laser element and a semi-reflective operating mirror 34 situated forwardly of the laser element so as to face a variable focusing lens 36. The mirrors of the optical resonator are disposed in the coaxial manner to a longitudinal axis A--A of the laser rod 26 and operating laser beam. The focusing lens 36 which is at least partially positioned within the housing 20 is typically operated by a micromotor on command from the control unit 18. A desired position of the focusing lens 36 can be also arranged manually by a medical personnel before or during a surgery. The optical resonator 30 is adopted to align and amplify the laser beam, whereas the focusing lens 36 directs it to the targeted area. In order to facilitate efficient delivery of the light energy from the exciting arrangement 28 to the operating laser element 26, the interior of the laser cavity can be covered by a material of high reflectivity.

A cooling arrangement 38 is provided within the housing 20 rearwardly of the laser cavity 22. The cooling arrangement can be of any known type producing an axial stream of gaseous coolant. In the preferred embodiment of the invention the cooling arrangement is a fan 38 which generates an axially directed air stream B extending longitudinally in the interior of the housing 20. In order to increase efficiency of the cooling process the exterior of the laser cavity 22 is formed with a plurality of ribs 40 extending outwardly therefrom. Thus, upon activation of the fan, axially directed air stream B is blown over the exterior of the laser cavity 22, including the ribs 40 reducing their temperature. The air stream B during its travel within the handpiece is directed through openings in the housing (not shown) to the exterior parts of the focusing lens 36, so as to prevent pollution of the lens by disintegrated skin products resulted from the surgery. Upon reaching the operated area of the skin, the air stream B also facilitates removal of the disintegrated tissue products form the site of the surgery and reduces effect of an unpleasant odor on medical personnel.

Longitudinal distribution of the elements of the invention within the housing 20 helps to reduce the dimensions and facilitates efficient delivery of the air coolant and reduction of temperature of the laser cavity and throughout the interior area of the handpiece. Furthermore, use of air cooling system results in better stability of temperature and other characteristics of the laser cavity, especially during and after multiple thermocycling.

The surgical apparatus 10 is energized through a source of standard electrical supply 42 or through a set of batteries 44. In order to eliminate any potential shock hazard specially upon switching the power from the source of standard electrical supply to the battery unit, a power interlock switch can be provided.

The power supply unit 14 generates electrical voltage pulses which are converted by the exciting arrangement or the flash lamp 28 into light pulses. In the laser cavity 22, after being directed to the laser rod 26, such light pulses are converted into laser pulses having shorter duration of emission compared to the voltage pulses. The wavelength of the laser irradiation is determined by the type of the laser rod or active element utilized by the surgical apparatus. In the preferred embodiment of the invention Er:YAG(erbium) laser is used as the active element or laser rod 26 of the surgical apparatus. The laser rod made of this material emits the electromagnetic energy corresponding to the wavelength of the "window of non-transparency" of water. The wavelength of this laser is 2.94 micron and is very close to the maximum absorption wavelength of water, which is about 3 mm. Thus, at this wavelength of the operating laser beam a great portion of its energy is absorbed by the operated living tissue which consists up to 90 percent of water.

The essential requirement for the materials used in the active element of the operating laser is that the wavelength of their irradiation belongs to the "window of non-transparency" region of the spectrum. Therefore, the laser medium of the active element of the invention can be selected from, but is not limited to, the following group of materials which forms a part of this category: $Y_3Al_5O_{12}:Nd$ (wavelength 1.33 micron):$Gd_3Ga_5O_{12}:Cr$, Ce, Nd (wavelength 1.42 micron); $MgF_2:Co$ (wavelength 1.75 micron); $BaYb_2F_8:Er$ (wavelength 2.0 micron); $LiYF_4:Er,Tm,Ho$ (wavelength 2.06 micron); $Y_3Sc_2Al_3O_{12}:Cr,Er$ (wavelength 2.8 micron); $(Y,Er)_3Al_5O_{12}$ (wavelength 2.94 micron); HF—chemical (wavelength 2.6-3.0 micron) and CO-gaseous (wavelength 5.0-6.0 microns).

This wavelength of the operating laser beam belongs to the infrared region of the spectrum and is invisible to the naked eyes of a surgical operator. In view of that, an operator can not observe the emission of the operating laser beam from the forefront of the handpiece. This might cause erroneous surgical steps raising serious questions of security in the medical treatment. To eliminate this drawback in the invention a guide light unit 46 generating a continuous, visible guide light beam is provided. Such guide light unit can be He:Ne laser, semiconductor laser, light-emitting diodes or any other suitable source of visible radiation. In the embodiment of the invention illustrated in FIG. 32 such guide light unit 46 is a semiconductor laser providing a very low power, continuous laser beam. Unlike the Er:YAG laser, the semiconductor laser emits the beam in the visible region of the spectrum. The guide light beam is adopted to indicate the focal point of the operating laser beam as a visible light spot before the operating laser beam is applied. That is the operating beam is applied to the same area as the guide light beam spot. Therefore, an operator can start the operating laser after the guide light beam spot appears at the desired location. Thus, the continuous guide light laser beam serves aiming function simplifying targeting of the invisible pulse operating beam. In use, upon activation of the operating laser as well as the guide lasers, the continuous and the pulse beams are delivered to the targeted area. The operating laser can be easily focused at the targeted area based on the image of the guide light laser there. The disintegrated skin products accumulated at the site of the surgery are ultimately removed and disposed by the suction unit 16.

In the embodiments of FIGS. 17 and 18 the suction unit is designed as a device independent from the handpiece and energized by the power supply unit 14 of the surgical device. Nevertheless, forming the suction unit as a part of the handpiece is also contemplated.

In the alternative embodiment the cooling arrangement can be positioned outside the handpiece. For instance, it can be associated with the power unit in such manner that a stream of cooling air is delivered to the interior of the handpiece through a flexible piping or similar arrangement.

In operation of the FIG. 32 embodiment, to excite the operating laser, high voltage is developed in the power supply unit 14 and applied across the flash lamp 28. In the laser cavity 22 the delivery of the light energy from the flash lamp is facilitated by the highly reflective interior surface thereof. The energy from the flash lamp 28 is absorbed by the medium of the laser rod 26, so that the molecules in the laser medium are transferred from the ground state to the excited state. As those molecules return to their ground state, they emit photons of a particular wavelength. Part of the light emanates from the laser rod. The light is returned to the rod by the mirrors 32 and 34. The returned photons react with molecules of the laser medium in the excited state to cause those molecules to return to the ground state and themselves emit photons of the particular frequency. Thus, the emitted photons are in phase with the photons striking the molecules and directed in the same direction as the original photons. In the operating laser the photons traveling between the mirrors 32 and 34 follow a specific path, so that the photons resonate in particular modes at common frequency and phase. Eventually, the light between the mirrors 32 and 34 reaches such level of intensity that its substantial amount passes through the semi-reflective mirror 34 and is directed by the focusing lens 36 to the targeted area of the skin of a patient as operating beam.

Figure 33:
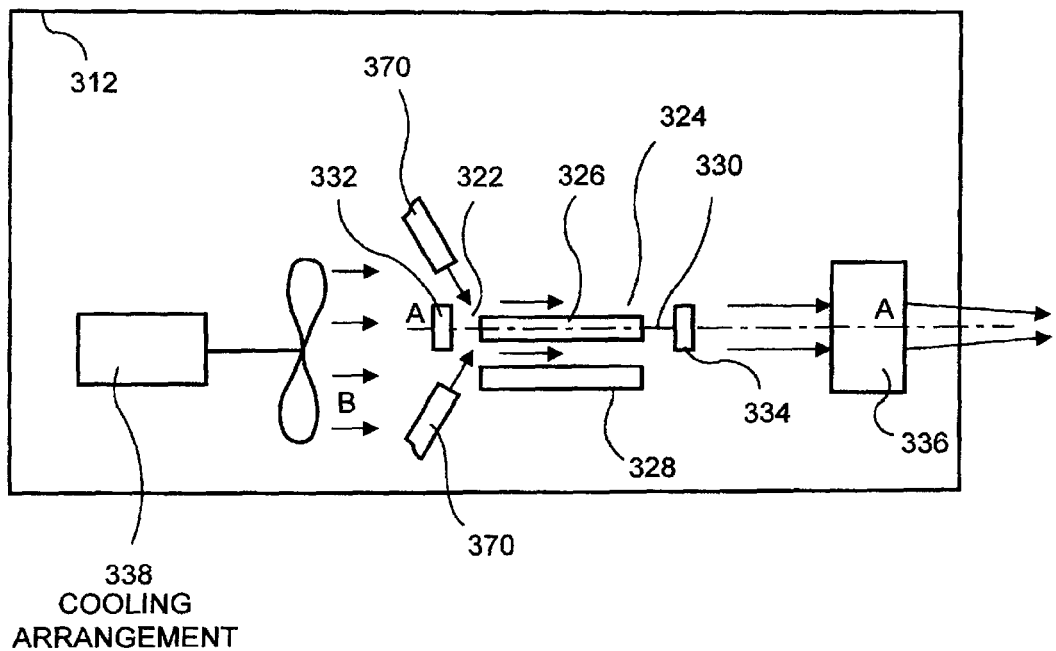
FIG. 33. shows another cooling arrangement of the invention.

FIG. 33 illustrates the embodiment of the invention in which the laser surgical device is formed with two working cavities. An auxiliary cavity 17 is associated with the power supply unit 14. This cavity contains the exciting arrangement such as a flash lamp 28 and is connected through an activated fiber optic arrangement 19 to a main laser cavity 15. Similar to the embodiment of the FIG. 32, the main laser cavity 15 contains the active element or laser rod 26 and the optical resonator 30 has two mirrors 32 and 24. In operation, high voltage developed in the power supply unit 14 is applied to the exciting arrangement 28 of the auxiliary cavity 17 generating impulses of light energy. These impulses are delivered to the active element 26 situated in the main cavity 15 by means of the activated fiber optic arrangement 19.

In the embodiment of FIG. 33 the high voltage pulses energizing the flash lamp 28 are not transmitted directly to the handpiece. Instead, such high voltage pulses are delivered to the auxiliary cavity 17 situated remotely from the handpiece and an operator. This provides even higher degree of safety for the surgical device of the invention since chances of electrical shock hazards to the medical personal are effectively minimized.

Furthermore, since the exciting arrangement or the flash lamp 28 is positioned outside of the main cavity, the weight of the handpiece is greatly reduced simplifying manipulations of the device by a surgeon.

It is best illustrated in FIGS. 17 and 18 that during a surgery the condition of operated tissue is monitored by a detecting arrangement or detector 48 adopted to detect irradiation reflected from that tissue. One of the main functions of the detector 48 is to control the effect of the operating laser beam on the skin of a patient in general and specifically to control the depth of penetration of the operating laser beam and the depth of vaporization of the epidermis. In every individual case a doctor sets specific characteristics of the laser irradiation to produce the required effect. If a predetermined depth of penetration of layer of a skin are achieved, the detector 48 generates a signal directed to the control unit 18 which in turn produces a correcting signal to the power unit or other units of the surgical device. Similar signals can be also produced when the prearranged levels of the energy density, power density or other characteristics of the operating laser are attained. This is necessary to exclude possibility of deeper penetration of the operating laser beam an/or damaging an adjacent healthy skin tissue. The intensity of the reflected light radiation from the skin of a patient depends upon such factors as: type and stage of a disease, color of a skin, general condition of a patient, the depth of a treated skin layer, etc. For each individual patient, considering the initial level of optical irradiation, such value of intensity characterizes a condition of an area of the skin treated by the laser surgical device of the invention. The detecting arrangement 48 can be made utilizing a wide variety of photosensitive elements, photoresistors, photodiodes and similar devices. If a photosensitive element is used to form the detector 48, the light reflected from the targeted area of the skin produces a flow of electrons in the photosensitive element directed towards its cathode and generates an electrical current or control signal for forwarding to the control unit 18. When photoresistors are utilized, the electrical resistance of the detector 48 varies depending upon the level of intensity of the light reflected from the operated tissue and received by the detector 48. The signal to the control unit 18 is based on such resistance.

FIG. 34 schematically illustrates a part of the laser assembly of another embodiment of the invention in which only portions of the active element and optical resonator are positioned in the main working cavity 21 situated in the handpiece. To accommodate such arrangement an auxiliary cavity 23 is provided. The exciting arrangement 28 and a first or auxiliary part 25 of the active element are situated within the auxiliary laser cavity 23. A distal end 29 of the first part 25 of the active element faces the mirror 32 having high reflectivity, whereas a proximal end thereof 31 is positioned at an end 37 of the light guide 41. To facilitate efficient delivery of the light energy from the exciting arrangement 28 to the first portion 25 of the active element the interior of the auxiliary cavity can be formed from a material having high reflective properties. A second or working part 27 of the active element and a semi-reflective mirror 34 of the optical resonator are situated in the main working cavity 21. The distal end 33 of the second part 27 of the active element and the proximal end 31 of the first part thereof are optically connected through a fiber light guide 41. Both ends of the light guide situated in the vicinity of the active element can be manufactured as parts of the optical resonator. In this respect, the end 37 of the light guide positioned in the auxiliary cavity 23 can be formed as a mirror having characteristics facilitating passage of the laser irradiation form the first part 25 towards the second part 33 of the active element. To facilitate the required operating laser beam operation form the main cavity 21, the end 39 of the light guide situated there inside can be formed as a mirror enabling passage of irradiation only in the direction of the second passage of irradiation only in the direction of the second part 27 of the active element. As in the previously discussed embodiment of FIG. 33, an operator is provided with an instrument devoid of electrical shock hazard and having considerably reduced weight. This is an important advantage of the present invention especially during prolonged surgical operations.

Figure 20:
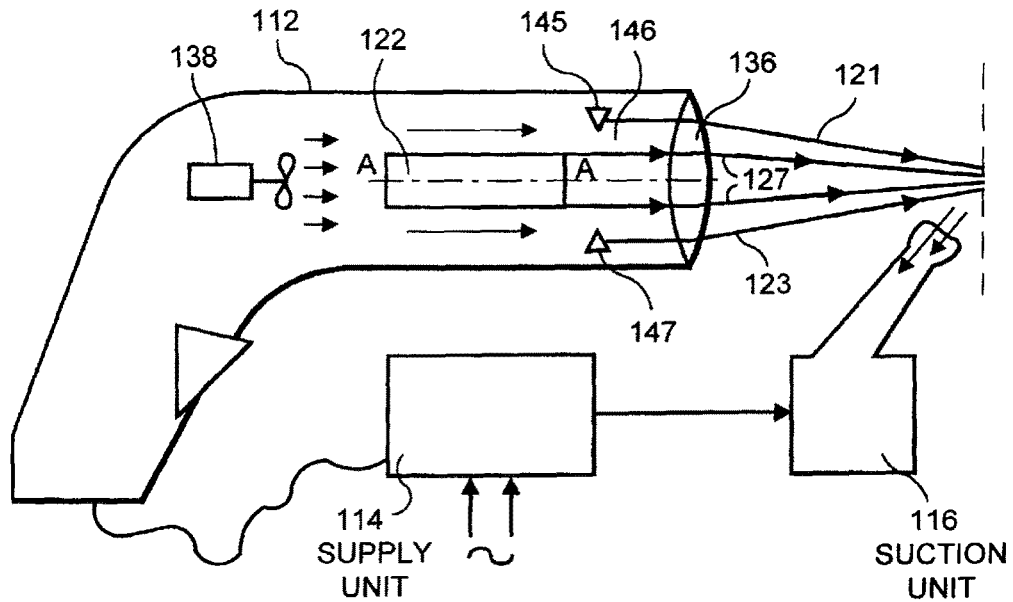
FIG. 20 shows a simplified embodiment of the laser surgical device.
Figure 21:
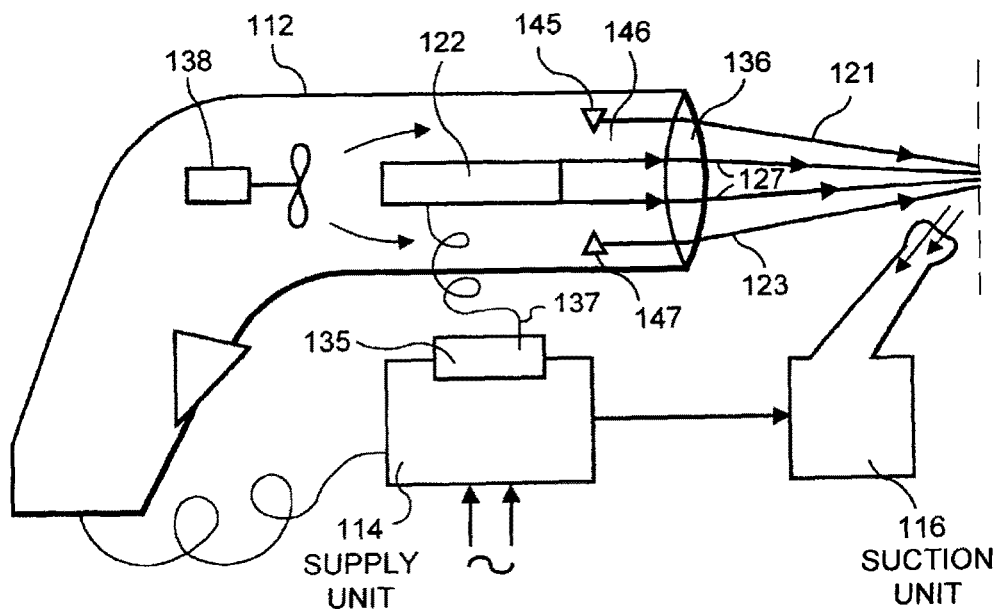
FIG. 21 shows another simplified embodiment of the laser surgical device.
Figure 35:
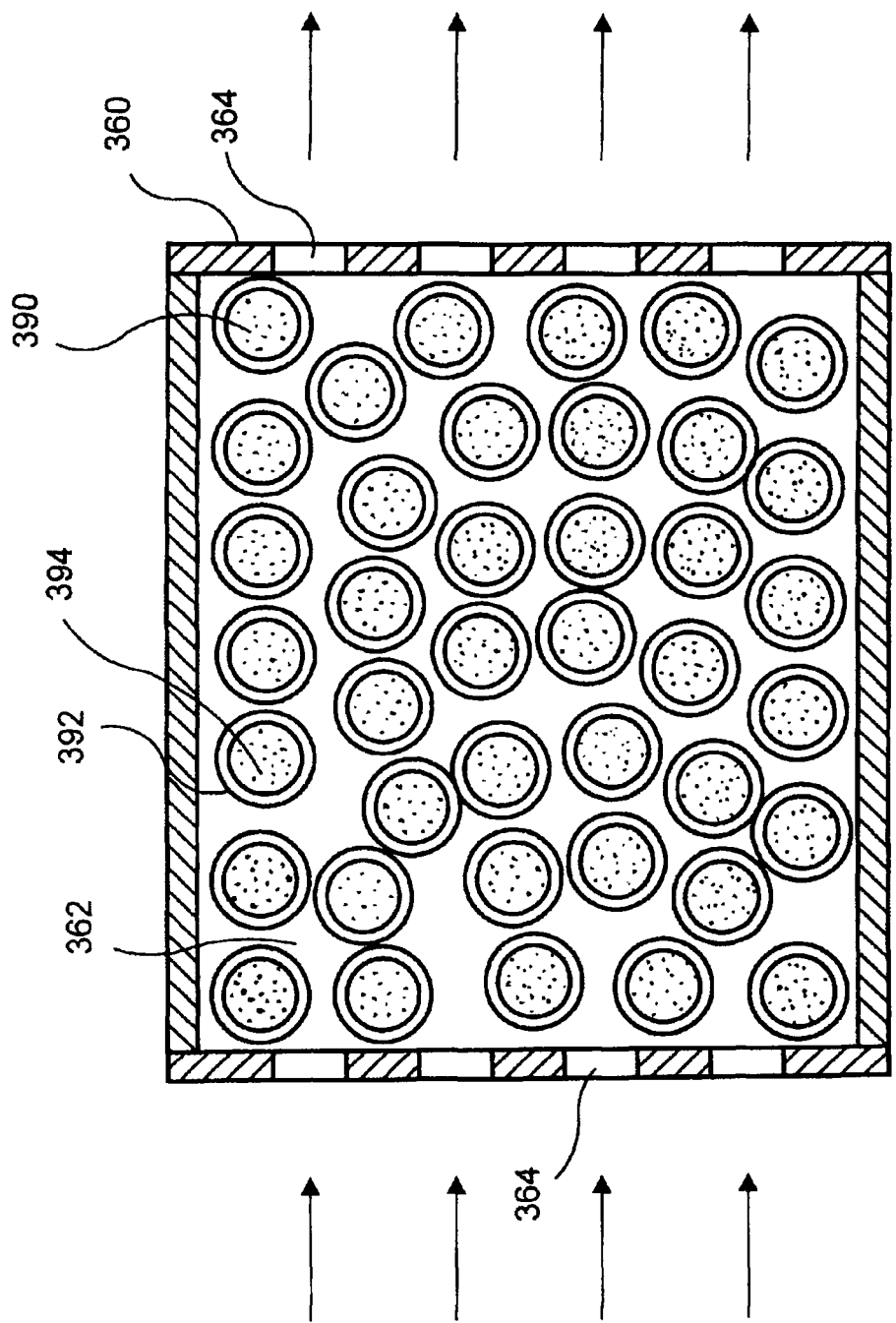
FIG. 35. illustrates positioning of the cooling elements within the interior chamber of the precooling unit.

A further simplified embodiment of the laser surgical device is best illustrated in FIGS. 20 and 21. It is shown in FIG. 35 that a handpiece 112 which resembles a housing of a hair drier contains an operating pulse laser 122, a cooling fan 138 and a light guide arrangement 146. In order to provide an axial air flow directed toward a patient, the fan 138 is positioned rearwardly of the operating laser. Two light-emitting diodes 145 and 147 of the light guide arrangement 146 are installed within the housing between the operating laser and the focusing lens 136. The light-emitting diodes are arranged in such a manner that the distance between the images of their light guide beams 121 and 123 in the focal plane of the focusing lens 136 is substantially equal to the diameter of the spot of the operating beam 127 of the operating laser 122 in this plane. Therefore, the targeted area of the operating beam spot can be identified by watching the visible images of the light guide beams. The dimensions of this operating beam spot can be adjusted by changing the distance between such visible images. The power supply unit 114 energizes not only the laser, fan and light guide arrangement but also the suction unit 116 positioned outside the housing. For the safety reasons all power feeding cables can be jacketed by earthen metal hoses. The pulse rate and the pulse energy of the operating laser 122 are set manually be generating a command from the control panel of the power supply unit 114. Similar to previously described embodiments, the suction unit 116 provides removal of the fragments of the disintegrated particles of skin developed during the surgery. The focusing lens 136 can be made of a quarts glass.

Figure 36:
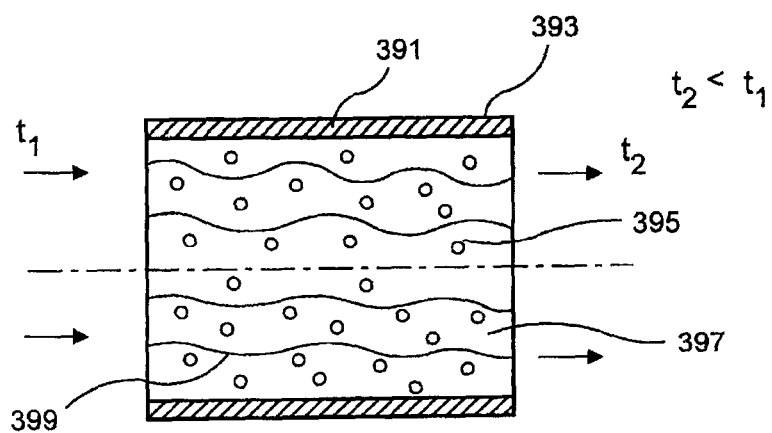
FIG. 36. illustrates a cooling capsule of the invention.

The laser surgical device of FIG. 36 is similar to that of FIG. 35. However, in FIG. 36 the exciting arrangement 135 is positioned outside the handpiece 112 and the impulses of light energy are delivered to the operating laser 122 by means of a light guide 137. In this respect, the instrument of FIG. 36 operates in a manner similar to the embodiment of FIG. 33. The modified embodiment of FIG. 36 in which a portion of the active laser element or rod is situated outside of the handpiece (see FIG. 34) is also contemplated.

In the embodiments illustrated in FIGS. 20 and 21 the focusing lens 136 is moved manually a predetermined distance. During such movement the position of images generated by the light-emitting diodes 145 and 147, which determine the size of the operating laser spot in the focal plane, is automatically changed.

Figure 26:
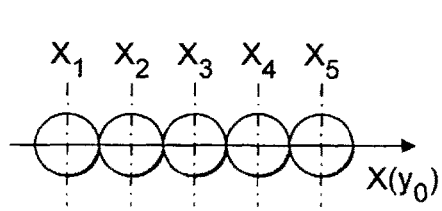
FIGS. 26 and 27 illustrate different patterns of laser beam images.
Figure 27:
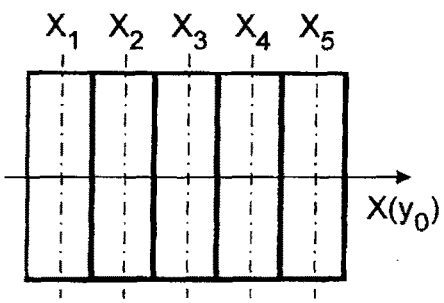

If the motion of the lens 136 is provided in the direction substantially perpendicular to the operating beam axis A--A, a series of laser beam images may be obtained in the focal plane. For example, FIG. 26 illustrates this condition for the normal and FIG. 27 for cylindrical lenses.

Figure 28:
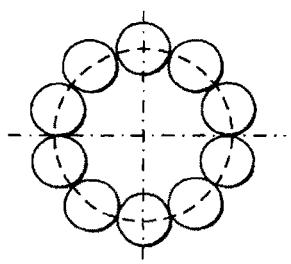
FIGS. 28 and 29 illustrate further patterns of laser beam images.
Figure 29:
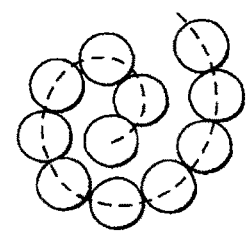
Figure 30:
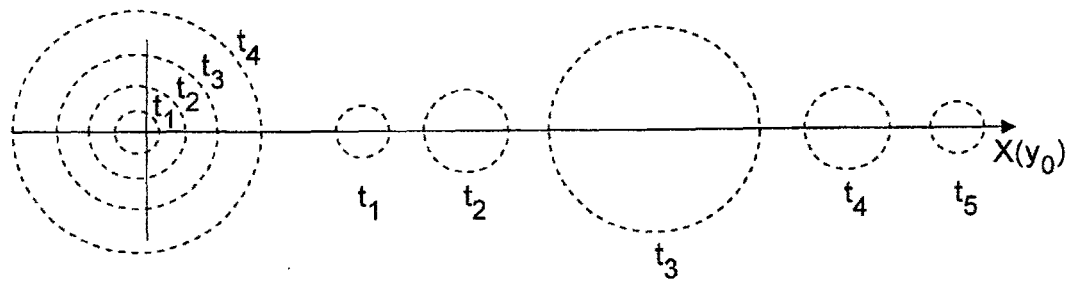
FIG. 30 illustrates conditions of beam scanning at a preset program.
Figure 31:
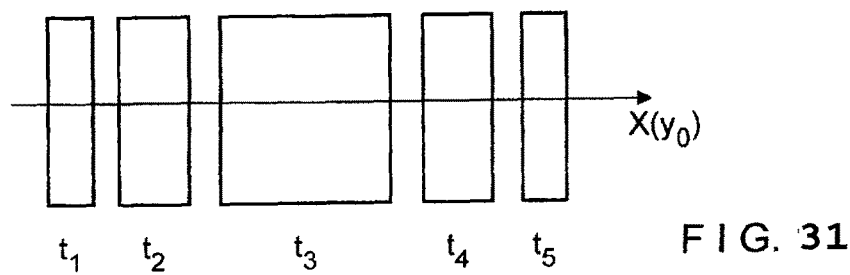
FIG. 31 illustrates conditions of beam scanning when the laser beam is in the slot form.

Upon motion of the focusing lens in the direction parallel to the axis of the beam it is possible to obtain a more complex image pattern, i.e. circular (see FIG. 28), spiral patterns (see FIG. 29).

Figure 22:
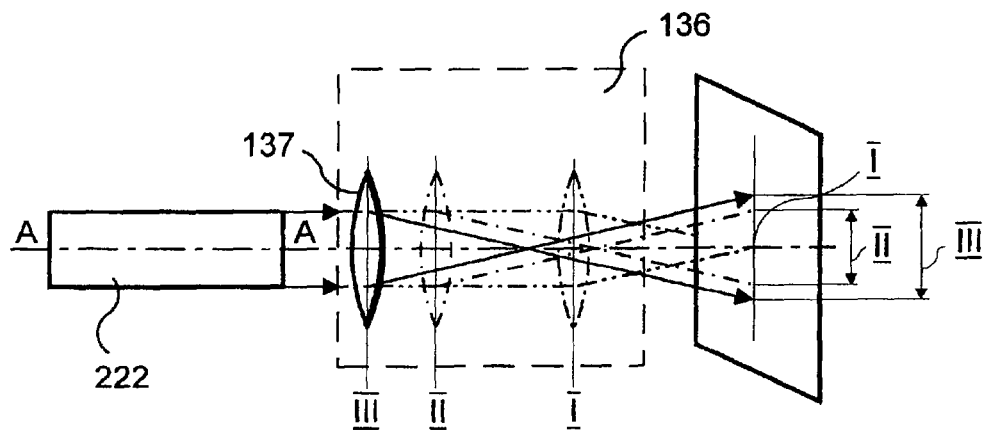
FIG. 22 illustrates alternative positions of the lens of focusing arrangement.

Depending upon the type of operation, replacement of the focusing lens is possible in the present invention. Typically the most suitable lens is one having an optical element smoothly traveling along the axis of the operating laser beam, so that the optical element can be fixed at a prearranged intermediate position. In this respect, FIG. 22 illustrates the focusing lens 137 having three such intermediate positions.

The size of the operating laser spot in the focusing region can be regulated by a microdevice upon a signal from the control unit 18 (see FIG. 32). This can be also accomplished manually by an operator or according to a prearranged program. Thus, the size of the operating laser spot of the operating laser beam can be adjusted in the focal plane of the focusing lens up to the sizes at which irregularities of the laser spot are still acceptable.

The focusing lens shown in FIG. 23 produces the operating beam in the form of an oblong strip. This is achieved by using a semi-cylindrical lens 237. The required changes in the form of this strip can be provided by rotating and guiding the lens 237 in a predetermined fashion.

The embodiment of the focusing lens 236 illustrated in FIG. 24 enables the invention to produce a trace of movement of the focused operating laser beam in the form of a ring. This is achieved by rotating the focusing lens 236 about its axis B--B which is shifted a predetermined distance C from the axis A--A of the operating laser beam.

Figure 25:
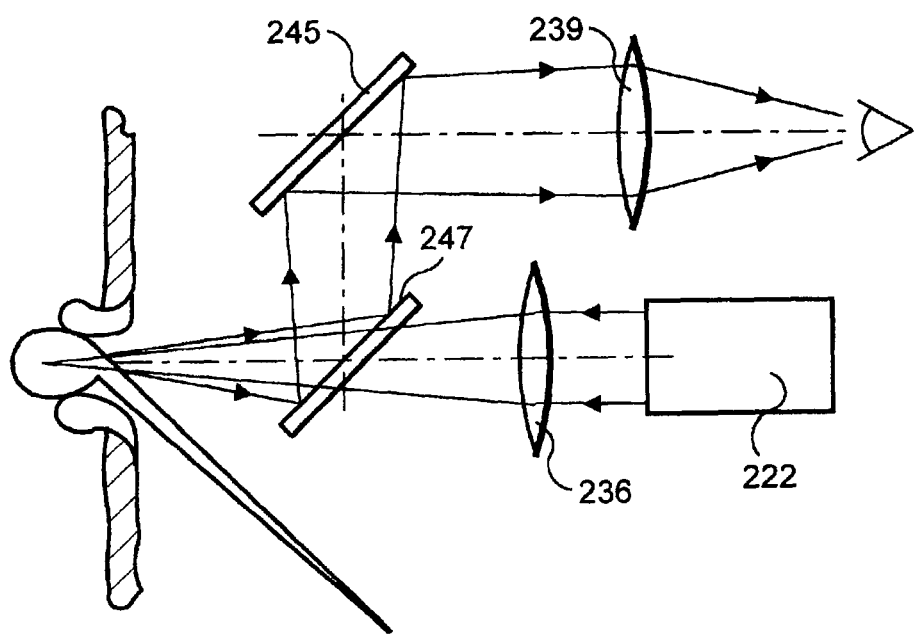
FIG. 25 shows application of an accessory lens to the laser surgical device.

As to the embodiment of FIG. 25, it illustrates a supplemental focusing lens for the precise focusing of the operating laser beam of the targeted area. For this purpose it is advisable initially to fixedly attach the laser assemble 222 with the lenses 236, 239 and the mirrors 245, 247 at the prearranged condition. The visible guide light should be prealigned with the invisible operating laser beam. In this case it is desirable to keep stationary at least a part of the patients body which is the subject of a surgery. A special device can be provided to accomplish this task.

The surgical device of the invention utilizes laser irradiation within the entire spectrum of the wavelength corresponding to the "window of non-transparency" of water. At the density of the laser irradiation of the operating beam spot 5-10 J/cm 2 and the diameter of the operating laser beam spot 3-10 mm, the depth of penetration of the operating laser beam of the invention into the epidermis does not exceed 10-20 microns. This occurs upon application of impulses having a very short duration of about 0.001 sec. After dehydration of the tissue, the spot of the operating laser beam produces only local vaporization of the top layer of the skin of a patient. This occurs without damaging in depth as well as superficially healthy regions of epidermis surrounding the operated area. The treated area of the tissue can be increased by moving the spot of the operating laser beam over the surface of the skin. The depth of penetration of the operating laser beam into the living tissue can be manipulated by changing the frequency of the electromagnetic impulses. Typically, during a session having duration of 30-60 seconds about 50-100 impulses are provided.

The laser surgical device of the invention can be also utilized for disinfecting lesions by scattered infrared laser emission. The density of this type of emission does not produce damage to normal healthy skin. However, such emission eliminates staphylococcal colonies in the skin area damaged by a disease.

The optical system of the laser surgical device also enables a user to perform surgical operations which are followed by the laser photocoagulation and laser dissection including ablation of cancerous tumors. The present invention also facilitates removal of a benign tumor by vaporization of one layer of tissue at a time. This task can be accomplished through application of several laser impulses having a predetermined spot area to each part of the skin affected by the disease. The treatment is continued until "blood dew" appears on the skin and is typically followed by a course of drug treatment.

To achieve proper results, a temperature of the active laser element during operation of the surgical device should be substantially minimized. For example, when the laser medium YAG:ER is utilized as the active element the temperature of the laser element should not exceed 44.degree. C.

The apparatus of the invention is capable of compensating natural deterioration of laser characteristics by gradual increase of the level of energy delivered to the laser element. The control unit 18 described hereinabove with reference to FIGS. 17 and 18, can be utilized for this purpose. The control unit 18 by measuring the intensity of the laser signals reflected from the operated area of the patient's body makes required corrections in the level of energy delivered by the power unit to the laser element.

To compensate for the deterioration of laser characteristics, the control unit of the device can provide constant increase of the energy level delivered by the power unit. However, unlimited increase of the delivered energy causes undesirable raise of temperature which might cause damage to the laser element. To prevent such undesirable event, the temperature distortions in the laser element resulted from the excessive power delivery have to be minimized or eliminated. Thus, after a time interval of an interrupted operation, the laser element has to be shut down until the temperature distortions disappear. Therefore, time of uninterrupted performance of the surgical laser element is often substantially limited. In some instances, interruptions up to 2-5 minutes are required during the surgery. In practice however, many surgeries demand uninterrupted performance of the laser element for about 15-30 minutes.

In the apparatus of the invention, the above discussed drawbacks can be alleviated by reduction of temperature of the fluid coolant used for cooling of the laser element. For example, this can be accomplished by utilizing coolants having a high lever of thermal calorific capacity.

In one embodiment of the laser surgical device of the invention, a precooling unit 360 is provided. As illustrated in FIG. 32, the precooling unit 360 includes an interior chamber 362 which communicates with the interior of the laser housing and an outside environment through openings 364 provided in its outer walls. In the embodiment of FIG. 32, the precooling unit 360 is positioned upstream of the cooling arrangement or fan 338. The interior chamber 362 is adapted to receive solid or semi-solid concentrated coolant 365 having a high level of thermal calorific capacity. An example of such concentrated coolant is solid carbon dioxide (dry ice) or regular ice. In case of carbon dioxide, partial vaporization of the concentrated coolant leads to the increased concentration of carbon dioxide in the air stream initially passing through the precooling unit and delivered to the laser element 322 situated within the laser cavity. Such stream of mixed coolant has a temperature substantially lower than the ambient temperature. Thus, the temperature of the gaseous coolant surrounding the operational laser element 322 will be substantially reduced.

This enables the laser element of the invention to generate a laser beam of required intensity and characteristics for longer time intervals without the necessity to increase energy delivered to the laser element by the power unit. Such arrangement also enables the invention to provided better stability of the laser characteristics.

A solid piece of carbon dioxide 366 situated in the interior chamber 362 of the precooling unit can be formed with a plurality of passages 365 (See FIG. 32). Thus, in view of suction generated by the cooling fan 338 within the interior of the laser chamber, a stream of ambient air before entering the interior of the housing passes through the passages 365 in the solid carbon dioxide. This arrangement increases time and surface of contact between the concentrated coolant and the air stream passing through the precooling unit and ultimately enhances the efficiency of the cooling process.

The solid concentrated coolant can be in the form of multiple pieces situated within the interior chamber 362 of the precooling unit. Thus, a stream of ambient air prior to entering the interior region of the laser housing travels between the plurality of pieces of the solid concentrated coolant, such as for example, solid carbon dioxide.

Although, use of a concentrated coolant in the form of a solid carbon dioxide has been described herein above, it should be understood that use of any form of concentrated coolant in the precooling unit is within the scope of the invention.

For example, a regular ice can be utilized in the precooling unit of the invention. The ice in the above described manner can be formed with passages facilitating passage of air stream therethrough. Furthermore, a plurality of pieces of ice can be also positioned within the interior chamber of the precooling unit.

Another embodiment of the precooling arrangement, is illustrated in FIG. 35. In this embodiment, the interior chamber 362 contains a plurality of cooling elements 390. Each cooling element 390 can be in the form of a substantially hollow member having exterior 392 and interior 394 portions. The exterior portion of each member is made of a material having high thermal conductivity for example, metals. On the other hand, the interior of the spherical element is filled with materials having high thermal calorific capacity. Examples of such materials are ethane, bromine, etc. In use, a temperature of a gas stream passing through a plurality of cooling elements 390 is substantially lowered prior to entering the interior of the laser housing.

The precooling device can be adapted to receive a capsule 391 (see FIG. 36). The capsule is formed with an exterior wall 393 surrounding an interior region thereof 395. The exterior wall is made of a material having low heat conductivity, whereas the inner region of the capsule is formed from a material having a high level of thermal calorific capacity. A plurality of axially extending channels are developed in the inner region of the capsule, so as to facilitate passage of a cooling gas stream therethrough. The inner walls of the channels are made from a material having a high level of heat conductivity. To lower the temperature, the air or gas stream passes through the passages of the capsule prior to entering the interior of the laser housing.

In use, prior to conducting a surgery, the capsule is placed into a refrigerator or a reservoir having a very cold temperature. Upon lowering the temperature of the capsule, it is removed from the refrigerator and positioned in the interior chamber of the precooling unit. Thus, an airstream prior to entering the laser housing, passes through the channels in the capsule. Therefore, the temperature of the airstream at the entrance in the housing will be substantially lowered.

A similar technique is used with cooling elements 390 illustrated in FIG. 36.

FIGS. 33 and 34 illustrate the embodiments of the invention in which the concentrated coolant is a gas having thermal calorific capacity higher than that of ambient air. For example, such gas can be $CO_2$.

As illustrated in FIG. 33, the gaseous coolant is introduced into the airstream generated by a fan in the direct vicinity of the operating laser element. In this instance, the precooling unit includes cooling outlets 370 positioned within the housing and situated in the vicinity of the operating laser element 326. The stream of gaseous coolant directly engages the surface of the laser element bypassing such obstacles as mirrors 332, 334 of the optical resonator.

In the embodiments of FIGS. 32 and 33, the airstream is generated by the fan 338. Such airstream is distributed within the entire interior of the housing. Thus, only a part of this airstream is directly utilized for cooling of the laser element. Therefore, in order to increase the efficiency of the cooling process, the airstream has to be concentrated in the vicinity of the laser element. In order to generate a substantial pressure required for efficient passage of the gaseous coolant within the gap, a compressor means is provided. Such compressor is typically positioned outside of the housing so that the gaseous coolant is delivered from the compressor through the pipeline to the gas outlets situated in the direct vicinity of the gap.

As illustrated in FIG. 34, a source of gaseous coolant 380 can be situated outside of the laser housing. A compressor or air pump can be used for delivery of gaseous coolant to the interior of the laser chamber through a pipeline 382 and an inlet arrangement 384. In the embodiment of FIG. 34, the gaseous coolant can be delivered directly to the laser element in a manner similar to the arrangement of FIG. 33. The precooling arrangements as described hereiabove with reference to FIGS. 32, 35, and 36, can be installed in the embodiment of FIG. 34, between the compressor 380 and the inlet arrangement 384.

Thus the pressurized gas streams are precooled before entering the laser housing.

The liquefied gases can also be utilized as coolants in the laser surgical device of the invention.

While this invention has been described in terms of certain embodiment thereof, it is not intended that it be limited to the above description, but rather only to the extent set forth in the following claims. The embodiments of the invention in which an exclusive property or privilege is claimed are defined in the appended claims.

The teaching of the following references are incorporated herein by reference:

Foreign References

TABLE-US-00001 Publication Number Country Date IPC Class Germany December 1992 DE04119024A1 WO08908529 World Intellectual March 1989 Property Organization (WIPO)

Other References

C. V. Shank, R. Yen, and C. Hirlimann, "Time-Resolved Reflectivity Measures of Femtosecond-Optical-Pulse-Induced Phase Transitions in Silicon", Physical Review Letters, vol. 50, No. 6, 454-457, Feb. 7, 1983. C. V Shank, R. Yen, and C. Hirlimann, "Femtosecnd-Time-Resolved Surface Structural Dynamics of Optically Excited Silicon", Physical Review Letters, vol. 51, No. 10, 900-902, Sep. 5, 1983. C. V. Shank and M. C. Downer, "Femtosecond Dynamics of Highly Excited Semiconductors", Mat. Res. Soc. Symp. Proc, vol. 51, 15-23, 1985. S. Kuper and M. Stuke, "Femtosecond uv Excimer Laser Ablation", Applied Physics B, vol. 44, 199-204, 1987. S. Preuss, M. Spath, Y. Zhang, and M. Stuke, "Time Resolved Dynamics of Subpicosecond Laser Ablation", Applied Physics Letters, vol. 62, No. 23, 3049-3051, Jun. 7, 1993. A. M. Malvezzi, N. Bloembergen, and C. Y. Huang, "Time-Resolved Picosecond Optical Measurements of Laser-Excited Graphite", Review Letters, vol. 57, No. 1, 146-149, Jul. 7, 1986. D. H. Reitze, X. Wang, H. Ahn, and M. C. Downer, "Femtosecond Laser Melting of Graphite", Physical Review B, vol. 40, No. 17, Dec. 15, 1989. F. Muller, K. Mann, P. Simon, J. S. Bernstein, and G. J. Zaal, "A Comparative Study of Decomposition of Thin Films by Laser Induced PVD with Femtosecond and Nanosecond Laser Pulses", SPIE, vol. 1858, 464-475, 1993. International Search Report Form PCT/ISA/210 Dated 31 Jul. 1995 and Mailed 4 Aug. 1995. M. W. Berns et al., "Laser Microsurgery in Cell and Developmental Biology", Science, vol. 213, No. 31, 505-513, July 1981. G. L. LeCarpentier et al., "Continuous Wave Laser Ablation of Tissue: Analysis of Thermal and Mechanical Events", IEEE Transactions on Biomedical Engineering, vol. 40, No. 2, 188-200, February 1993. C. LeBlanc, "Realization and Characterization of a High Intensity Femtosecond Laser System Based on all Titanium Doped Sapphire", Annales de Physique, vol. 19, No. 1, Abstract, February 1994. R. Birngruber, C. Puliafito, A. Gawande, W. Lin, R. Schoenlein, and J. Fujimoto, "Femtosecond Laser-Tissue Interactions: Retinal Injury Studies", IEEE Journal of Quantum Electronics, vol. QE-23, No. 10, 1836-1844, October 1987. B. Zysset, J. Fujimoto, and T. Deutsch, "Time-Resolved Measurements of Picosecond Optical Breakdown", Applied Physics B 48, 139-147 (1989). B. Zysset, J. Fujimoto, C. Puliafito, R Birngruber, and T. Deutsch, "Picosecond Optical Breakdown: Tissue Effects and Reduction of Collateral Damage", Lasers in Surgery and Medicine 9:192-204(1989). S. Watanabe, R. Anderson, S. Brorson, G. Dalickas, J. Fujimoto, and T. Flotte, "Comparative Studies of Femtosecond to Microsecond Laser Pulses on Selective Pigmented Cell Injury in Skin", Photochemistry and Photobiology vol. 53, No. 6, 757-762, 1991). N. Bloembergen, "Laser-Induced Electric Breakdown in Solids", IEEE Journal of Quantum Electronics, vol. QE-10, No. 3, (March 1974). R Birngruber, C. Puliafito, A. Gawande, W. Lin, R. Schoenlein, and J. Fujimoto, "Femtosecond Laser-Tissue Interactions: Retinal Injury Studies", IEEE Log No. 8716039, (1987). D. Stern, R. Schoenlein, C. Puliafito, E. Dobi, R. Birngruber, and J. Fujimoto, "Corneal Ablation by Nanosecond, Picosecond, and Femtosecond Lasers at 532 and 625 nm", Arch Ophthalmol, vol. 107, (April 1989). J. Squier, F. Salin, and G. Mourou, "100-fs Pulse Generation and Amplification in Ti:Al2 03", Optics letters, vol. 16, No. 5, (March 1991). B. Frueh, J. Bille, and S. Brown, "Intrastromal Relaxing Excisions in Rabbits with a Picosecond Infrared Laser", Lasers and Light in Ophthalmology, vol. 4, No. 3/4, (1992), 165-168 R. Remmel, C. Dardenne, and J. Bille, "Intrastromal Tissue Removal Using an Infrared Picosecond Nd:YLF Ophthalmic Laser Operating at 1053 nm", Lasers and Light in Ophthalmology, vol. 4, No. 3/4, 169-173, (1992). J. Squier and G. Mourou, "Tunable Solid-State Lasers Create Ultrashort Pulses", Laser Focus World, (June 1992). M. H. Niemz, T. P. Hoppeler, T. Juhasz, and J. Bille, "Intrastromal Ablations for Refractive Corneal Surgery Using Picosecond Infrared Laser Pulses", Lasers and Light in Ophthalmology, vol. 5, No. 3, pp. 149-155 (1993). H. Cooper, J. Schuman, C. Puliafito, D. McCarthy, W. Woods, N. Friedman, N. Wang, and C. Lin, "Picosecond Neodymium: Yttrium Lithium Fluoride Laser Sclerectomy", Am. Journal of Opth. 115:221-224, (February 1993). K. Frederickson, W. White, R. Wheeland, and D. Slaughter, "Precise Ablation of Skin with Reduced Collateral Damage Using the Femtosecond-Pulsed, Terawatt Titanium-Sapphire Laser", Arch Dermatol, vol. 129, (August 1993). H. Kapteyn and M. Murnane, "Femtosecond Lasers: The Next Generation", Optics & Photonics News, (March 1994). G. Mourou, A. Zewail, P. Barbara, and W. Knox, "New Generation of Ultrafast Sources Marked by Higher Powers, Versality", Optics Photonics News, (March 1994). D. Du, X. Liu, G. Korn, J. Squier, and G. Mourou, "Laser-Induced Breakdown by Impact Ionization in SiO2 with Pulse Widths from 7 ns to 150 fs", Appl. Phys. Lett 64 (23), (Jun. 6, 1994). Optics, Eugene Hecht et al., Addison-Wesley Publishing Company, 1979.

The teachings of the following United States patents (US patents); World Intellectual Property Organization patents (WO patents); Japanese patents (JP patents); European Patent Office patents (EP patents) and patents of other foreign jurisdictions (DD, DE, GB, RU, SU) are incorporated herein by reference. The methods and apparatus described herein can be advantageously utilized in the methods and apparatus of the incorporated references to achieve the enhanced properties and features described herein in the methods and apparatus of the incorporated references. For example where the reference uses a radiation beam, such as a light beam, in-particular a laser beam, the laser techniques according to the present invention can be used. The laser pulse of the present invention can be directed for example by using a light pipe or a wave guide. Commonly available, such as commercially available, light pipes and wave guides can be used.

TABLE-US-00002 U.S. Pat. Nos. 6,251,102 6,238,386 6,231,568 6,231,567 6,224,589 6,213,998 6,200,311 6,190,377 6,152,919 6,066,127 5,951,543 5,893,828 5,868,731 5,860,426 5,783,798 5,725,523 5,688,263 5,658,275 5,611,797 5,607,420 5,571,098 5,562,658 5,549,600 5,534,000 5,454,808 5,403,306 5,397,327 5,366,456 5,346,489 5,312,396 5,290,279 5,269,778 5,224,942 5,219,347 5,195,541 5,194,712 5,180,378

5,163,935 5,154,708 5,125,923 5,098,427 5,092,864
5,074,861 5,004,338 4,963,143 4,950,268 4,939,336
4,862,886 4,846,171 4,832,979 4,812,613 4,791,927
4,791,926 4,790,310 4,788,975 4,736,743 4,729,373
4,702,245 4,693,244 4,669,465 4,658,817 4,638,800
4,633,872 4,627,435 4,597,380 4,592,353 4,580,557
4,573,466 4,573,465 4,566,453 4,564,012 4,550,240
4,532,400 4,519,390 4,517,973 4,503,854 4,497,319
4,491,131 4,478,217 4,473,074 4,470,414 4,469,098
4,459,986 4,408,602 4,273,109 4,270,845 4,266,549
4,266,548 4,266,547 4,249,533 4,240,431 4,233,493
4,185,633 4,174,154 4,144,888 4,143,660 4,141,362
3,910,276 3,906,953 3,865,114 3,865,113 3,858,577
3,123,066
TABLE-US-00003 WO patents 0,141,871 0,128,447 0,110,304 0,115,592 0,113,812 0,113,810 0,106,908 0,019,920 0,110,288 0,108,576 0,108,579 0,078,242 0,054,686 0,048,525 9,965,405 9,955,243 9,955,218 9,951,156 9,944,518 9,900,062 9,818,394 9,713,468 9,715,236 9,612,441 9,410,923 9,325,156 9,314,432 9,312,727 9,311,699 9,221,299 9,217,138 9,208,427 9,206,641 9,203,977 9,012,619 8,704,610 8,606,642 8,505,263 8,505,262 8,500,010
TABLE-US-00004 JP patents 2001054524 2001029359 2001008946 2001008945 11104147 10328196 10113354 08229049 09010221 09000537 08299352 08148737 07124169 06090959 05220167 05220166 05220101 05176938 04023339 04129545 03278489 03139346 03041943 02239857 02099048 01320050 01036650 01034347 63318935 60104902 59195891 58145901 58087887 58084887 56114390 55083011 55083010
TABLE-US-00005 EP patents 1097676 0717964 0669107 0423431 0458506 0391976 0372362 0327410 0341943 0297360 0292622 0069351
TABLE-US-00006 Other patents DD217711 DD258360 DE2646029 DE4030240 GB2214084 GB2274724 RU2113827 RU2090157 RU2077274 RU2045935 STJ570233

We claim:

1. A laser apparatus for use in a surgical procedure comprising:
    a housing having interior and exterior regions, said housing forming a part of a handpiece adapted for positioning in a hand of an operator;
    a laser cavity extending within said interior region of the housing, an operating laser element generating an operating beam, at least a portion of said operating laser element being positioned within the interior region of the housing;
    a controller configured to remove a first biological tissue from the surface of a second biological tissue using laser induced breakdown of the first biological tissue by plasma formation with said operating beam by focusing said operating beam to a location above a plane of said first biological tissue for ablation of said first biological tissue by said operating beam.

2. The apparatus according to claim 1 further comprising:
    a cooling arrangement generating a stream of a first coolant,
    a precooling unit containing a second semi-solid coolant formed with at least one passage going therethrough, and
    said cooling arrangement communicating with said precooling unit in such a manner that said stream of the first coolant before entering the interior of the housing passes through said at least one passage so as to form a stream of mixed coolant within the interior region of the housing.

3. The apparatus of claim 2, wherein at least a portion of said precooling unit is situated outside of said housing.

4. The apparatus of claim 3, wherein said semi-solid coolant is carbon dioxide or dry ice.

5. The apparatus of claim 4, wherein said precooling unit includes a chamber adapted for receiving said semi-solid carbon dioxide, said chamber communicating with the interior of the housing, and said cooling arrangement is a fan generating a stream of gaseous coolant containing particles of carbon dioxide within the interior region of the housing.

6. The apparatus of claim 5, wherein said fan generates suction within the interior region of the housing in such a manner that a stream of ambient air before entering the interior of the housing passes through said at least one passage in said carbon dioxide.

7. The apparatus according to claim 1 wherein:
    a. said beam comprises one or more laser pulses in which each pulse has a pulse width equal to or less than a pulse width value corresponding to a change in slope of a curve of fluence breakdown threshold (Fth) as a function of laser pulse width (T), said change occurring at a point between first and second portions of said curve, said first portion spanning a range of relatively long pulse width where Fth varies with the square root of pulse width ($T^{1/2}$) and said second portion spanning a range of short pulse width relative to said first portion with a Fth versus T slope which differs from that of said first portion; and
    b. an optical system focusing said one or more pulses of said beam to a point above the surface of the tissue to cause laser induced break down of the tissue.

8. The apparatus according to claim 7 further comprising:
    a cooling arrangement generating a stream of a first coolant,
    a precooling unit containing a second semi-solid coolant formed with at least one passage going therethrough, and
    said cooling arrangement communicating with said precooling unit in such a manner that said stream of the first coolant before entering the interior of the housing passes through said at least one passage so as to form a stream of mixed coolant within the interior region of the housing.

9. A laser apparatus for use in a surgical procedure comprising:
    a housing having interior and exterior regions, said housing forming a part of a handpiece adapted for positioning in a hand of an operator;
    a laser cavity extending within said interior region of the housing; an operating laser element generating an operating beam, at least a portion of said operating laser element being positioned within the interior region of the housing;
    a controller configured to remove a first biological tissue from the surface of a second biological tissue using laser induced breakdown of the first biological tissue with the operating beam by focusing the operating beam to a point above a surface of the first biological tissue so that the operating beam defines a spot and has a lateral gaussian profile characterized in that fluence at or near the center of the beam spot is greater than a threshold fluence whereby the laser induced breakdown is ablation by said operating beam of an area within the spot.

10. The apparatus according to claim 9 further comprising:
a cooling arrangement generating a stream of a first coolant,
a precooling unit containing a plurality of pieces of a second semi-solid concentrated coolant, and
said cooling arrangement communicating with said precooling unit in such a manner that said stream of the first coolant before entering the interior of the housing passes between said plurality of pieces of said second coolant.

11. The apparatus of claim 10, wherein said second concentrated coolant consists of a plurality of pieces of semi-solid carbon dioxide situated within a chamber of the precooling unit, said cooling arrangement generates suction within the interior region of the housing, so that a stream of ambient air prior to entering the interior region of the housing passes between said plurality of pieces of semi-solid carbon dioxide.

12. The apparatus of claim 10, wherein said cooling arrangement communicates with said precooling unit in such a manner that said stream of the first coolant entrains particles of said second semi-solid coolant, so as to form a stream of mixed coolant within the interior region of the housing, said mixed coolant having thermal calorific capacity higher than the thermal calorific capacity of the first coolant.

13. The apparatus according to claim 9 wherein:
a. said beam comprises one or more laser pulses in which each pulse has a pulse width equal to or less than a pulse width value corresponding to a change in slope of a curve of fluence breakdown threshold (Fth) as a function of laser pulse width (T), said change occurring at a point between first and second portions of said curve, said first portion spanning a range of relatively long pulse width where Fth varies with the square root of pulse width (T½) and said second portion spanning a range of short pulse width relative to said first portion with a Fth versus T slope which differs from that of said first portion; and
b. an optical system focusing said one or more pulses of said beam to a point above the surface of the tissue to cause laser induced break down of the tissue.

14. A laser apparatus for use in a surgical procedure on tissue comprising:
a housing having interior and exterior regions, said housing forming a part of a handpiece adapted for positioning in a hand of an operator;
a laser cavity extending within said interior region of the housing, an operating laser element generating an operating beam, at least a portion of said operating laser element being positioned within the interior region of the housing;
a controller configured to remove a first biological tissue from the surface of a second biological tissue by plasma formation with said operating beam by focusing said operating beam to a region above a surface of said first biological tissue and spaced apart from said first biological tissue to induce breakdown by plasma formation in said first biological tissue.

15. The apparatus according to claim 14 further comprising:
a cooling arrangement generating a stream of a first coolant,
a precooling unit containing a second solid concentrated coolant in the form of a plurality of independent cooling members, and
said cooling arrangement communicating with said precooling unit in such a manner that said stream of the first coolant before entering the interior of the housing passes between said plurality of independent cooling members.

16. The apparatus according to claim 15, wherein at least a portion of said cooling arrangement is situated within an interior part of the handpiece.

17. The apparatus of claim 15, wherein said second concentrated coolant includes a plurality of independent members situated within a chamber of the precooling unit, said cooling arrangement generating suction within the interior region of the housing, so that a stream of ambient air prior to entering the interior region of the housing passes between said plurality of independent members.

18. The apparatus of claim 15, wherein each of said independent cooling members is formed having exterior and interior portions, each said exterior portion is made of a material having high thermal conductivity and each said interior portion is made of a material having high thermal calorific capacity.

19. The apparatus of claim 15, wherein said precooling unit includes a chamber adapted for receiving said plurality of independent cooling members, said chamber communicates with the interior of the housing, said cooling arrangement is a fan generating a stream of gaseous coolant passing between said plurality of independent cooling members prior to entering the interior of the housing.

20. The apparatus according to claim 14 wherein:
a. said beam comprises one or more laser pulses in which each pulse has a pulse width equal to or less than a pulse width value corresponding to a change in slope of a curve of fluence breakdown threshold (Fth) as a function of laser pulse width (T), said change occurring at a point between first and second portions of said curve, said first portion spanning a range of relatively long pulse width where Fth varies with the square root of pulse width (T½) and said second portion spanning a range of short pulse width relative to said first portion with a Fth versus T slope which differs from that of said first portion; and
b. an optical system focusing said one or more pulses of said beam to a point above the surface of the tissue to cause laser induced break down of the tissue.

* * * * *